United States Patent
Poleksic

(10) Patent No.: US 6,988,039 B2
(45) Date of Patent: Jan. 17, 2006

(54) METHOD FOR DETERMINING SEQUENCE ALIGNMENT SIGNIFICANCE

(75) Inventor: Aleksandar Poleksic, Pasadena, CA (US)

(73) Assignee: Eidogen, Inc., Pasadena, CA (US)

( * ) Notice: Subject to any disclaimer, the term of this patent is extended or adjusted under 35 U.S.C. 154(b) by 0 days.

(21) Appl. No.: 10/367,583

(22) Filed: Feb. 14, 2003

(65) Prior Publication Data

US 2004/0167720 A1 Aug. 26, 2004

(51) Int. Cl.
 *G06F 17/00* (2006.01)

(52) U.S. Cl. .......................................... 702/19; 702/20
(58) Field of Classification Search .................. 702/19, 702/20
See application file for complete search history.

(56) References Cited

PUBLICATIONS

MPSRCH User/Reference Manual, Version 2.0, Dec. 1994, IntelliGenetics, Inc., Mountain View, CA, USA, pp. 104–109.

*Primary Examiner*—James Martinell
(74) *Attorney, Agent, or Firm*—Michael J. Wise, Esq.; Perkins Coie LLP

(57) ABSTRACT

The present invention relates to methods and systems for quickly determining the statistical significance of a raw alignment score produced by aligning a first sequence to a second sequence. The claimed methods and systems determine multiple estimates of the p-value of an alignment score. Each p-value estimate is then compared to a predefined threshold p-value. Depending upon the claimed method employed and further depending upon whether a particular p-value estimate is less than/greater than the threshold p-value, a raw alignment score may be considered statistically significant or insignificant.

57 Claims, 7 Drawing Sheets

METHOD FOR DETERMINING SEQUENCE ALIGNMENT SIGNIFICANCE

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A COMPUTER PROGRAM APPENDIX

Not Applicable

FIELD OF THE INVENTION

The invention relates to the field of computational methods for determining genomic sequence relationships.

BACKGROUND OF THE INVENTION

The human genome contains somewhere between 50,000 and 150,000 genes. Current efforts to identify protein drug targets focus on a small number of "drug-proven" protein families such as kinases, proteases, nuclear hormone receptors, transmembrane proteins, chemokines, and cytokines. These protein families are referred to as "drug-proven" because a number of proven drugs and validated, screened targets are based upon proteins found in these families. In order to maximize the number of new drugs brought to market (currently, only about 5% of drug development projects reach the market) many companies are directing their efforts on identifying and characterizing novel members of drug-proven protein families through genome wide sequence homology searching.

Sequence alignment methods are applicable to genomic and proteomic sequences and attempt to identify the function of a given sequence by detecting the similarity of a query sequence to other sequences of known structure or function. To the extent a sequence is homologous to another sequence it may be expected that either the two genes, two gene products or proteins share similar structural and functional characteristics. Accordingly, if the known gene expression product is a drug target, homology modeling methods may be used to identify the genes/cDNA sequences corresponding to novel potential drug targets. Further, to the extent the structure and function of the known target has been characterized by other techniques, such as determination of the target's biological function, its three-dimensional structure, or the presence/absence of active sites or protein-protein interaction sites, similar structural and functional assignment may be made to the potential drug target.

Among its uses for target identification and characterization, sequence comparison methods may be used for determining gene function maps by comparing the sequences of complete cDNA copies or cDNA fragments of known function against genomic DNA. Gene function maps may be used for developing DNA binding drugs which turn on/off a gene or gene cluster.

Homology modeling based upon sequence comparison methods may be used to identify and characterize the function, three-dimensional structure and active regions of potential protein drug targets by comparing the sequence relatedness, or the sequence homology, between complete cDNA copies or cDNA fragments of known protein drug targets against complete cDNA copies or cDNA fragments of unknown gene expression products.

Sequence comparison methods, BLAST algorithms, Hidden Markov Models and the various Smith-Waterman based techniques assign an alignment score based upon the sequence similarity of two sequences. An unnormalized, raw alignment score is calculated based upon residue substitution probabilities, residue insertion/deletion penalties and background residue probabilities. The highest scoring alignment between two sequences is referred to as the optimal alignment.

In order to assure that an alignment score is statistically meaningful—i.e. to show the degree a particular alignment score varies from the alignment score expected from aligning two random sequences—it is necessary to normalize a raw alignment score. In the art, one of the most common measures for representing whether a raw alignment score is statistically meaningful is with the p-value of the alignment score. The p-value of a raw alignment score, x, gives the probability of finding an alignment with score S of at least x for the alignment of two randomly selected sequences of the same length as those sequences which produced the alignment score x. It has been shown that when gaps are not allowed and in the limit of large sequence lengths m and n, the p-value of score x may be represented as:

$$P(S \geq x) \approx 1 - \exp(-Kmne^{-\lambda x}) \qquad 1$$

where $\lambda$ and K are scaling parameters. Karlin, S. and Altschul, S. F., *Methods for assessing the statistical significance of molecular sequence features by using general scoring schemas*, Proc. Natl. Acad. Sci. USA, 87 (1990), pp. 2264–2268; Dembo, A., Karlin, S. and Zeitouni, O., *Limit distribution of maximal non-aligned two-sequence segmental score*, Ann. Prob., 22 (1994), pp. 2022–2039. These references and each other reference herein are hereby incorporated in their entirety as if fully set forth herein. Many computational experiments suggest that the same formula applies to the statistics of gapped sequence alignments. In this case, $\lambda$ and K must be established from a large scale comparison of random sequences. $P(S \geq x)$ will be referred to throughout as $P(x|K,\lambda)$.

A number of approximations have been employed to estimate $P(S \geq x)$. The latest version of PSI-BLAST, which is generally regarded as the most sensitive of the BLAST algorithms, pre-calculates the scaling parameters A and K using Island statistics, for a plurality of randomly generated sequence pairs of varying length, a plurality of substitution matrices and a plurality of gap penalties. The residue frequency in the random sequences is chosen to reflect background residue frequencies. For each query/template sequence pair, PSI-BLAST calls the look-up table and selects a particular set of pre-calculated $\lambda$ and K parameters based upon the similarity in length of the query/template sequences to the random generated sequences and further based upon the identity of the gap scoring and substitution matrices employed for the template/query pair. While PSI-BLAST's look-up table is computationally efficient to generate, its efficiency comes at the cost of accuracy. More particularly, it assumes background residue frequency and the granularity in length sampling and gap penalties introduce further errors. Greater accuracy could be achieved if $\lambda$ and K are determined for each query/template pair that is aligned, but only at the cost of substantially slowing a PSI-BLAST search.

Island Method

The Island method is a computationally efficient method for determining λ and K and thereby determining Function 1 from a plurality of Smith-Waterman matrices. Olsen, R., Bundschuh, R., and Hwa, T., *Rapid assessment of external statistics for gapped local alignments, Proceedings of the Seventh International Conference on Intelligent Systems* (AAAI Press, Menlo Park, Calif., 1999), pp. 211–222. The value of each cell in a Smith-Waterman matrix corresponds to the highest scoring local alignment that ends at that particular cell. An 'island' consists of all those cells connected to a common anchor cell. The score assigned to an island is the maximum score of the cells that comprise the island.

The Island method generates a large number of island scores from a plurality of Smith-Waterman matrices formed from either 1) aligning multiple randomly selected sequences; or 2) aligning multiple residue 'shuffles' of the same two sequences. Since Equation 1 becomes increasingly accurate for larger values of x, improved estimates of λ may be obtained by only considering those islands with a score at least c. Altschul, S. F., Bundschuh, R., Olsen, R., and Hwa, T., *The estimation of statistical parameters for local alignment score distributions, Nucleic Acids Research*, 29-2 (2001), pp. 351–361. Altschul et al. have shown that the maximum-likelihood estimate of λ for the case of discrete alignment scores may be expressed as:

$$\hat{\lambda} = \ln\left(1 + \frac{1}{\overline{S}_c}\right) \quad 3$$

$$\overline{S}_c = \frac{1}{N}\sum_{i \in I_c} [S(i) - c] \quad 4$$

where S(i) is the score of the i'th island, $I_c = \{i | S(i) \geq c\}$ and $N = |I_c|$. For the case of continuous scores, such as found when aligning sequence profiles, $$\hat{\lambda} = \frac{1}{\overline{S}_c}.$$

Altschul et al. have also shown that the maximum likelihood estimate for K may be expressed as:

$$\hat{K} = \frac{R_c e^{\hat{\lambda} c}}{A} \quad 5$$

where A is the aggregate search area of the island search space. For example, if two sequences, of length m, and n, were compared once, A=mn. If B such comparisons were made, A=Bmn. For the sake of simplicity, the following examples and discussion will assume continuous alignment scores and use $$\hat{\lambda} = \frac{1}{\overline{S}_c}.$$

The present invention relates to an improved method of performing Island statistic based normalization of alignment scoring. More particularly, the present invention relates to a heuristic that efficiently uses Island statistics to quickly determine the statistical significance or insignificance of a raw alignment score produced by aligning a first sequence, usually the query sequence, to a second sequence, the template sequence. Because the methods of the present invention do not require 'look-up' tables a significant improvement in alignment sensitivity may be gained when a large database of template sequences is screened. Since the methods of present invention are independent of the alignment scoring scheme, sequence lengths and their composition, the methods are generally applicable to any dynamic programming based alignment method that considers local alignments. Accordingly, the claimed methods may be used equally by BLAST, PSI-BLAST, FASTA, HMMER or Eidogen's STRUCTFAST method disclosed in U.S. patent application Ser. No. 09/905,176.

SUMMARY OF THE INVENTION

Figure 1:
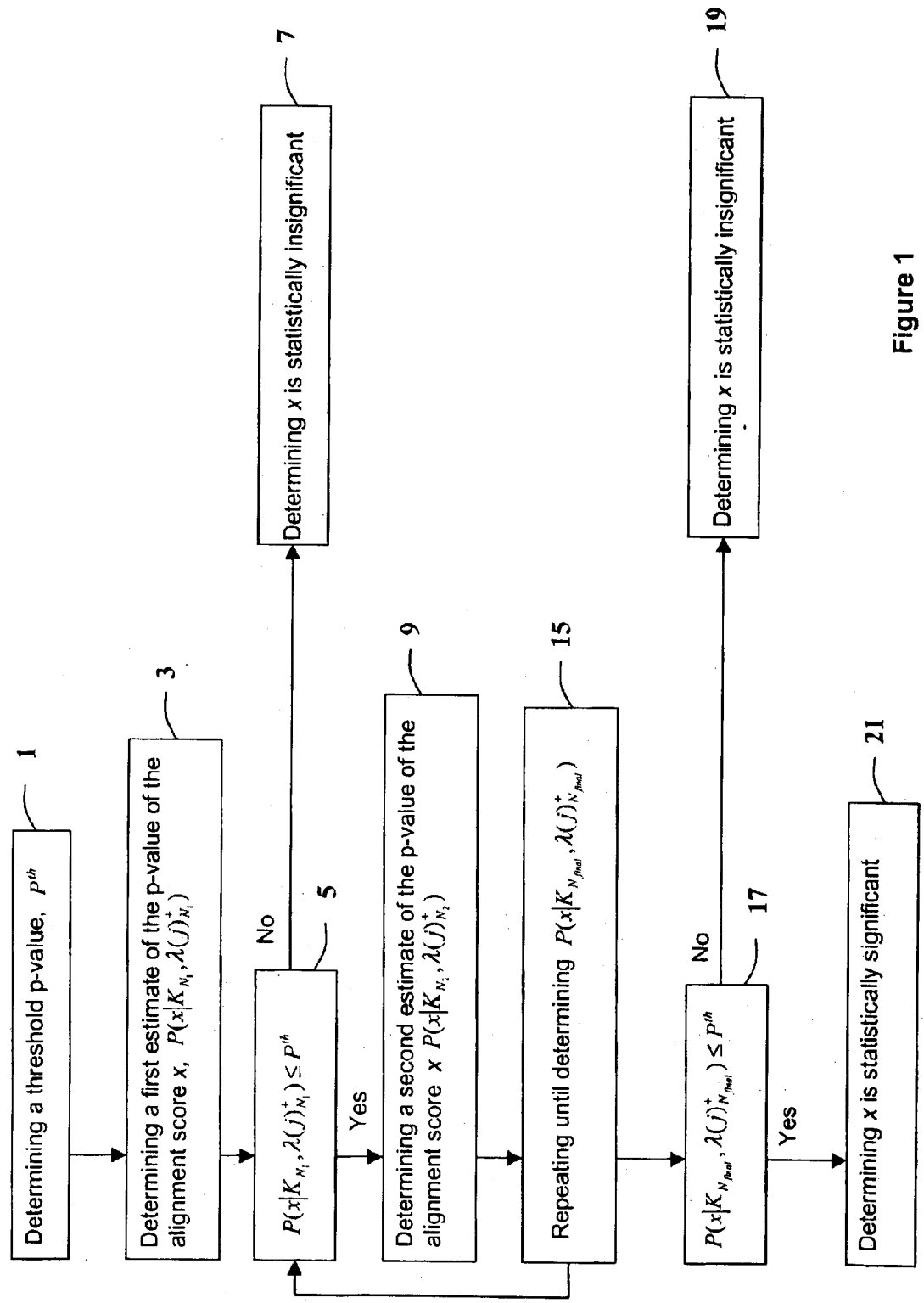
FIG. 1—illustrates one method according to the invention for quickly determining the statistical significance or insignificance of a raw alignment score produced by aligning a first sequence to a second sequence.

The present invention relates to methods and systems for quickly determining the statistical significance of a raw alignment score produced by aligning a first sequence to a second sequence. The methods of the claimed invention may be preferably applied when a query sequence is aligned against a very large number of template sequences such as when a bioinformaticist is trying to determine whether a query sequence is related to any of the sequences in large sequence database such as the Protein Data Bank. Ordinarily, when such an alignment study is performed, the vast majority of the raw alignment scores are not statistically significant. Accordingly, the claimed methods will allow those alignment scores that are statistically insignificant to be quickly determined without wasting expensive computational resources on calculating exact p-values.

The claimed methods and systems determine multiple estimates of the p-value of an alignment score. One method according to the invention, which may be preferably applied to quickly determine when an alignment score x produced from the alignment of a query sequence with a template sequence is statistically insignificant comprises the steps: 1) determining a threshold p-value, $P^{th}$; 2) determining a first estimate of the p-value of an alignment score x $P(x|K_{N_1},\lambda(j)_{N_1}^+)$; 3) comparing $P(x|K_{N_1},\lambda(j)_{N_1}^+)$ to $P^{th}$; and 4) if $P(x|K_{N_1},\lambda(j)_{N_1}^+) > P^{th}$, determining the raw alignment score x is statistically insignificant, otherwise determining the alignment score x may or may not be statistically insignificant. Another method according to the invention for quickly determining whether a raw alignment score x is statistically insignificant comprises the steps of: 1) determining a threshold p-value, $P^{th}$; 2) determining a first estimate of the p-value of the alignment score x, $P(x|K(\lambda(j)_{N_1}^+)_{N_1}^-,\lambda(j)_{N_1}^+)$; 3) comparing $P(x|K(\lambda(j)_{N_1}^+)_{N_1}^-,\lambda(j)_{N_1}^+)$ to $P^{th}$; and 4) if $P(x|K(\lambda(j)_{N_1}^+)_{N_1}^-,\lambda(j)_{N_1}^+) > P^{th}$, determining that the raw alignment score x is statistically insignificant, otherwise, determining the raw alignment score x may or may not be statistically insignificant.

The methods according to the invention use a plurality of estimates of the p-value of a raw alignment score x to iteratively determine whether x is significant or insignificant. Accordingly, another method according to the invention, that may be applied to quickly determine the statistical significance or insignificance of an alignment score x produced from the alignment of a query sequence with a template sequence comprises the steps: 1) determining a threshold p-value, $P^{th}$; 2) determining a first estimate of the p-value of the raw alignment score x, $P(x|K_{N_1},\lambda(j)_{N_1}^+)$; 3) comparing $P(x|K_{N_1},\lambda(j)_{N_1}^+)$ to $P^{th}$; 4) if $P(x|K_{N_1},\lambda(j)_{N_1}^+) \leq P^{th}$, determining a second estimate of the p-value of the raw alignment score x, $P(x|K_{N_2},\lambda(j)_{N_2}^+)$, where $N_2 \geq N_1$, otherwise, determining the alignment score-x is statistically insignificant; 5) repeating step 3) and step 4) until determining a final estimate of the p-value or raw alignment score x, $P(x|K_{N_{final}},\lambda(j)_{N_{final}}^+)$; 6) comparing $P(x|K_{N_{final}},\lambda(j)_{N_{final}}^+)$ to $P^{th}$ and 7) if $P(x|K_{N_{final}},\lambda(j)_{N_{final}}^+) \leq P^{th}$, determining the raw alignment score x is statistically significant otherwise, determining that the raw alignment score x is statistically insignificant.

Another method according to the invention for determining whether a raw alignment score x is statistically significant or insignificant comprises the steps of: 1) determining a threshold p-value, $P^{th}$; 2) determining a first estimate of the p-value of the raw alignment score x, $P(x|K(\lambda(j)_{N_1}^+)_{N_1}^-,\lambda(j)_{N_1}^+)$; 3) comparing $P(x|K(\lambda(j)_{N_1}^+)_{N_1}^-,\lambda(j)_{N_1}^+)$ to $P^{th}$; 4) if $P(x|K(\lambda(j)_{N_1}^+)_{N_1}^-,\lambda(j)_{N_1}^+) \leq P^{th}$, determining a second estimate of the p-value of raw alignment score x, $P(x|K(\lambda(j)_{N_2}^+)_{N_2}^-,\lambda(j)_{N_2}^+)$, where $N_2 \geq N_1$, otherwise, determining the alignment score x is statistically insignificant; 5) repeating steps 3) and 4) until determining a final estimate of the p-value of raw alignment score x, $P(x|K(\lambda(j)_{N_{final}}^+)_{N_{final}}^-,\lambda(j)_{N_{final}}^+)$; 6) comparing $P(x|K(\lambda(j)_{N_{final}}^+)_{N_{final}}^-,\lambda(j)_{N_{final}}^+)$ to $P^{th}$; and 7) if $P(x|K(\lambda(j)_{N_{final}}^+)_{N_{final}}^-,\lambda(j)_{N_{final}}^+) \leq P^{th}$, determining the alignment score x is statistically significant, otherwise, determining it is statistically insignificant.

Another method for quickly determining the statistical significance or insignificance of a raw alignment score comprising the steps of: 1) determining a threshold p-value, $P^{th}$; 2) determining a first estimate of the p-value of the raw alignment score x, $P(x|K(\lambda(j)_{N_1}^+)_{N_1}^+,\lambda(j)_{N_1}^-)$; 3) comparing $P(x|K(\lambda(j)_{N_1}^+)_{N_1}^+,\lambda(j)_{N_1}^-)$ to $P^{th}$; 4) if, $P(x|K(\lambda(j)_{N_1}^+)_{N_1}^+,\lambda(j)_{N_1}^-) > P^{th}$, determining a second estimate of the p-value of the raw alignment score x, $P(x|K(\lambda(j)_{N_2}^+)_{N_2}^-,\lambda(j)_{N_2}^+)$ where $N_2 = N_1$, otherwise, determining that the raw alignment score is statistically significant; 5) comparing $P(x|K(\lambda(j)_{N_2}^+)_{N_2}^-,\lambda(j)_{N_2}^+)$ to $P^{th}$; 6) if $P(x|K(\lambda(j)_{N_2}^+)_{N_2}^-,\lambda(j)_{N_2}^+) \leq P^{th}$, determining a third estimate of the p-value of the raw alignment score x, $P(x|K(\lambda(j)_{N_3}^+)_{N_3}^+,\lambda(j)_{N_3}^-)$, where $N_3 = N_1$, otherwise, determining the raw alignment score is statistically insignificant; 7) repeating steps 3) through 6) until determining a final estimate of the p-value of raw alignment score x, $P(x|K(\lambda(j)_{N_{final}}^+)_{N_{final}}^+,\lambda(j)_{N_{final}}^-)$; 8) comparing $P(x|K(\lambda(j)_{N_{final}}^+)_{N_{final}}^+,\lambda(j)_{N_{final}}^-)$ to $P^{th}$; and 9) if $P(x|K(\lambda(j)_{N_{final}}^+)_{N_{final}}^+,\lambda(j)_{N_{final}}^-) \leq P^{th}$, determining the raw alignment score x, is statistically significant, otherwise, determining it is insignificant.

In addition to the methods according to the invention, another aspect of the invention is a computer system programmed to perform the methods according to the invention.

DETAILED DESCRIPTION OF THE INVENTION

Methods According to the Invention

The claimed invention is based in-part upon the observations that:

1) If $\lambda_2 \leq \lambda_1$ and $K_2 \geq K_1$ then $P(x|K_2,\lambda_2) \geq P(x|K_1,\lambda_1)$. Accordingly, if an alignment score x is not statistically significant—i.e. if its p-value for a particular set of $\lambda_1$ and $K_1$ parameters (see Equation 1) exceeds a certain threshold value—then x will not be statistically significant for a second set of parameters $\lambda_2$ and $K_2$ if $\lambda_2 \leq \lambda_1$ and $K_2 \geq K_1$.

2) The distribution of $$\frac{\hat{\lambda}}{\lambda_{true}}$$

is normal. In the case of continuous scores, its standard deviation (standard error), may be represented as $$\frac{1}{\sqrt{N}}$$

with a mean of 1. For the case of finite alignment scores its standard error may be represented as $$\frac{e^\lambda - 1}{\lambda\sqrt{e^\lambda}} \frac{1}{\sqrt{N}}$$

with a mean of 1.

3) The distribution of $$\frac{\hat{K}}{K_{true}}$$

is normal with a mean one. Its standard deviation may be represented as $\sqrt{K_{true}/Nmne^{-\lambda S}}$.

4) Observation 2 further implies that for the inequality, $$1 - j\sigma < \frac{\hat{\lambda}}{\lambda_{true}} < 1 + j\sigma,$$

where $\sigma$ is the standard error of $$\frac{\hat{\lambda}}{\lambda},$$

it is possible to assign a probability that the inequality is valid.

5)

$$1 - j\sigma < \frac{\hat{\lambda}}{\lambda_{true}} < 1 + j\sigma$$

may be rewritten for the case of continuous scores as $\lambda(j)_N^- < \lambda_{true} < \lambda(j)_N^+$ where $$\lambda(j)_N^- = \frac{\hat{\lambda}}{1 + \frac{j}{\sqrt{N}}}$$

and $$\lambda(j)_N^+ = \frac{\hat{\lambda}}{1 - \frac{j}{\sqrt{N}}}.$$

6) Similarly, observation 3 further implies that for the inequality, $$1 - j\sigma < \frac{\hat{K}}{K_{true}} < 1 + j\sigma,$$

where σ is the standard error of $$\frac{\hat{K}}{K_{true}},$$

it is possible to assign a probability that the inequality is valid.

7)

$$1 - j\sigma < \frac{\hat{K}}{K_{true}} < 1 + j\sigma$$

may be rewritten for the case of continuous alignment scores as $K(\lambda(j)_N^+)_N^- < K_{true} < K(\lambda(j)_N^+)_N^+$, where $$K(\lambda(j)_N^+)_N^- = \frac{\hat{K}}{1 + \frac{je^{\lambda(j)_N^+ x}}{\sqrt{Nmn}}} \text{ and } K(\lambda(j)_N^+)_N^+ = \frac{\hat{K}}{1 - \frac{je^{\lambda(j)_N^+ x}}{\sqrt{Nmn}}}.$$

The aforementioned observations serve as one or more bases for the fast alignment score normalization methods according to the invention. Since $P(x|K,\lambda)$ depends exponentially on K, but double exponentially on λ, accurate estimates of λ are more important to an accurate estimation of $P(x|K,\lambda)$ than are accurate estimates of K. For the sake of simplicity of presentation, all calculations herein are based upon continuous alignment scores as are produced from profile-profile alignments. One skilled in the art will generally appreciate the interchangeability between sequence-sequence alignments and profile-profile alignments. The present invention is completely applicable to both without limitation.

One method according to the invention, illustrated in FIG. 1, which may be preferably applied to quickly determine the statistical significance or insignificance of an alignment score x produced from the alignment of a query sequence with a template sequence comprises the steps: 1) determining 1 a threshold p-value, $P^{th}$; 2) determining 3 a first estimate of the p-value of the raw alignment score x, $P(x|K_{N_1},\lambda(j)_{N_1}^+)$; 3) comparing 5 $P(x|K_{N_1},\lambda(j)_{N_1}^+)$ to $P^{th}$; 4) if $P(x|K_{N_1},\lambda(j)_{N_1}^+) \leq P^{th}$, determining 9 a second estimate of the p-value of the raw alignment score x, $P(x|K_{N_2},\lambda(j)_{N_2}^+)$, where $N_2 \geq N_1$, otherwise, determining 7 the alignment score x is statistically insignificant; 5) repeating 15 steps 3) and 4) until determining a final estimate of the p-value of the raw alignment score x, $P(x|K_{N_{final}},\lambda(j)_{N_{final}}^+)$; 6) comparing 17 $P(x|K_{N_{final}},\lambda(j)_{N_{final}}^+)$ to $P^{th}$; and 7) if $P(x|K_{N_{final}},\lambda(j)_{N_{final}}^+) \leq P^{th}$ 21 determining the raw alignment score x is statistically significant, otherwise 19, determining that the raw alignment score x is statistically insignificant. While one skilled in the art will certainly appreciate that in general, $K_{N_1}$ and $\lambda(j)_{N_1}^+$ may be represented more generally as $K_{N_{1,K}}$ and $\lambda(j)_{N_{1,\lambda}}^+$ since it is not necessary that $N_{1,K}=N_{1,\lambda}$, for the sake of clarity of presentation, the case of $N_{1,K}=N_{1,\lambda}=N_1$ will be illustrated.

Determining a Threshold p-Value $P^{th}$

A first step 1 in a method according to the invention and illustrated in FIG. 1, determines a threshold p-value, $P^{th}$, for an alignment score x. In general, as the threshold p-value decreases, alignment scores must increase to be considered statistically meaningful. Accordingly, threshold p-values may be selected based upon the alignment sensitivity that is required for a particular inquiry and the size of the particular database that is being screened. For example, if a bioinformaticist is interested in screening a query sequence against a database of 1,000,000 template sequences to detect all those sequences which are distantly related to the query as defined by an alignment score x, a threshold p-value of $10^{-6}$ would correspond to an expectation value ("e-value") of one—i.e. that one template sequence in the database would produce an alignment score with the query of at least x. As a general rule, e-values of less than $10^{-3}$ correspond to closely related sequences, e-values between $10^{-3}$ and 10 correspond to distantly related or twilight sequences and e-values greater than 10 correspond to unrelated sequences. Thus, exemplary threshold p-values, for detecting closely related sequences may include those values, $$P^{th} \leq \frac{10^{-3}}{Z}$$

where Z refers to the number of template sequences in a database. Exemplary, threshold p-values for detecting distantly related sequences may include those values, $$\frac{10^{-3}}{Z} \leq P^{th} \leq \frac{10}{Z}.$$

Determining a First Estimate of the p-Value $P(x|K_{N_1},\lambda(j)_{N_1}^+)$

A second step 3 determines a first p-value $P(x|K_{N_1},\lambda(j)_{N_1}^+)$ for an alignment score x, using the Island method applied to a first set of $N_1$ islands. This second step further depends upon selecting $\lambda(j)_{N_1}^+$ based upon the statistical likelihood that $\lambda_{true} < \lambda(j)_{N_1}^+$. Since the full width half maximum of $$\frac{\hat{\lambda}}{\lambda_{true}}$$

increases with increasing j, the likelihood that $\lambda_{true} \leq \lambda(j)_{N_1}^+$ increases with increasing j. For example, with j=3, there is a 99.8% chance that $\lambda(3)_{N_1}^- < \lambda_{true} < \lambda(3)_{N_1}^+$. For higher values of j, the accuracy of p-value estimates is increased still further. $K_{N_1}$ may be determined using Equation 4 and thus, $$K_{N_1} = \frac{N_1 e^{\lambda_{N_1} c}}{Bmn}.$$

$N_1$, the number of islands used in the first estimate of the p-value for the alignment score x typically ranges between 100–1000, but may range as high 5,000. Since, $P(x|K_{N_1},\lambda(j)_{N_1}^+)$ serves as the first filter to identify many of the alignment scores which are not statistically significant, it is preferable to minimize the number of islands generated in order to preserve computational resources. In general, the number of islands in a Smith-Waterman matrix generally depends upon the sequence lengths and the scoring scheme. However, assuming typical sequence lengths of the query and each template of 300 residues and further assuming typical PSI-BLAST gap scoring schemes, 100 islands may be generated by less than 10 sequence randomizations and in many cases less than 5 sequence randomizations.
Comparing $P(x|K_{N_1},\lambda(j)_{N_1}^+)$ to $P^{th}$ A third step 5 compares $P(x|K_{N_1},\lambda(j)_{N_1}^+)$ to $P^{th}$. If 7 $P(x|K_{N_1},\lambda(j)_{N_1}^+) > P^{th}$ the raw alignment score produced by aligning the query sequence and the first template sequence may be considered statistically insignificant.

Determining a Second Estimate of the p-Value $P(x|K_{N_2},\lambda(j)_{N_2}^+)$

If $P(x|K_{N_1},\lambda(j)_{N_1}^+) \leq P^{th}$ 9, there is insufficient information to determine whether $P(x|K_{true},\lambda_{true}) > P^{th}$ and thus whether the raw alignment score between the query and first template may be disregarded as statistically insignificant. Accordingly, a fourth step 9 determines $P(x|K_{N_2},\lambda(j)_{N_2}^+)$ for a larger, second set of $N_2$ islands. Assuming that the first and second estimates of the p-value are used for filtering statistically insignificant alignment scores, $N_2$ typically ranges from 1000–3500 islands, but may range as high as 7,000.

Repeating Steps 3) and 4) Until Determining $P(x|K_{N_{final}},\lambda(j)_{N_{final}}^+)$ A fifth step repeats 15 the third and fourth steps an integer number of times. Accordingly, if $P(x|K_{N_{n-1}},\lambda(j)_{N_{n-1}}^+) \leq P^{th}$, where $n \geq 3$, there is still insufficient information to determine whether $P(x|K_{true},\lambda_{true}) > P^{th}$. A next step determines $P(x|K_{N_n},\lambda(j)_{N_n}^+)$ for a still larger, n'th set of $N_n$ islands where $N_n > N_{n-1}$. In a next step, $P(x|K_{N_n},\lambda(j)_{N_n}^+)$, is compared to $P^{th}$ using the same comparison scheme as detailed in the third and fourth steps. This iterative process 15 is repeated until a final estimate of the p-value of raw alignment score x is determined, $P(x|K_{N_{final}},\lambda(j)_{N_{final}}^+)$. The final estimate of the p-value of a raw alignment score x is selected such that $P(x|K_{N_{final}},\lambda(j)_{N_{final}}^+) \approx P(x|K_{true},\lambda(j)_{true}^+)$. Since the standard error in $$\frac{\hat{\lambda}}{\lambda_{true}}$$

decreases as $1/\sqrt{N}$, for N=9,000, $\hat{\lambda} \approx \lambda_{true}$. Thus, if n estimates of the p-values are made, the number of islands considered in each step will range from approximately 100 for $P(x|K_{N_1},\lambda(j)_{N_1}^+)$ to approximately 9,000 or more for the final estimate, $P(x|K_{N_{final}},\lambda(j)_{N_{final}}^+)$. There is no inherent limit on the number of p-value estimates that may be employed by the claimed methods. The number of p-value estimates that may be employed by claimed methods depends upon the available computational resources, the size of the database and the sensitivity of the search. Typically two to about ten p-value estimates may be employed. But, given sufficient computational resources thousands of estimates may be determined. Most of the sequences screened in a database will have no statistically meaningful alignment with a query sequence, and the first estimate of the p-value of a raw alignment score may serve as a useful filter for quickly determining many such statistically insignificant scores at a low computational overhead.

This suggests another method according to the invention. By performing steps 2–4, namely, determining estimates of the p-value of a raw alignment score and comparing that estimate to a threshold p-value, it is possible to rapidly determine whether a raw alignment score is statistically insignificant. More generally, steps 2–3 may be repeated a plurality of times with each estimate of the p-value being determined from a larger number of islands than the preceding estimate of the p-value.

It also follows that it is more computationally efficient to increase N non-linearly so that the first few p-value estimates use less than approximately 3,500 islands. Although in the case of only two estimates of the p-value being computed, the first estimate, $P(x|K_{N_1},\lambda(j)_{N_1}^+)$ may be determined from even 5000 islands.

Comparing $P(x|K_{N_{final}},\lambda(j)_{N_{final}}^+)$ to $P^{th}$

A final step 17, compares $P(x|K_{N_{final}},\lambda(j)_{N_{final}}^+)$ to $P^{th}$ using the same comparison rules as were employed in the third step 5. Accordingly, if $P(x|K_{N_{final}},\lambda(j)_{N_{final}}^+) \leq P^{th}$, the raw alignment score x may be considered statistically significant 21, otherwise, it is considered statistically insignificant 19.

EXAMPLE 1

Figure 2:
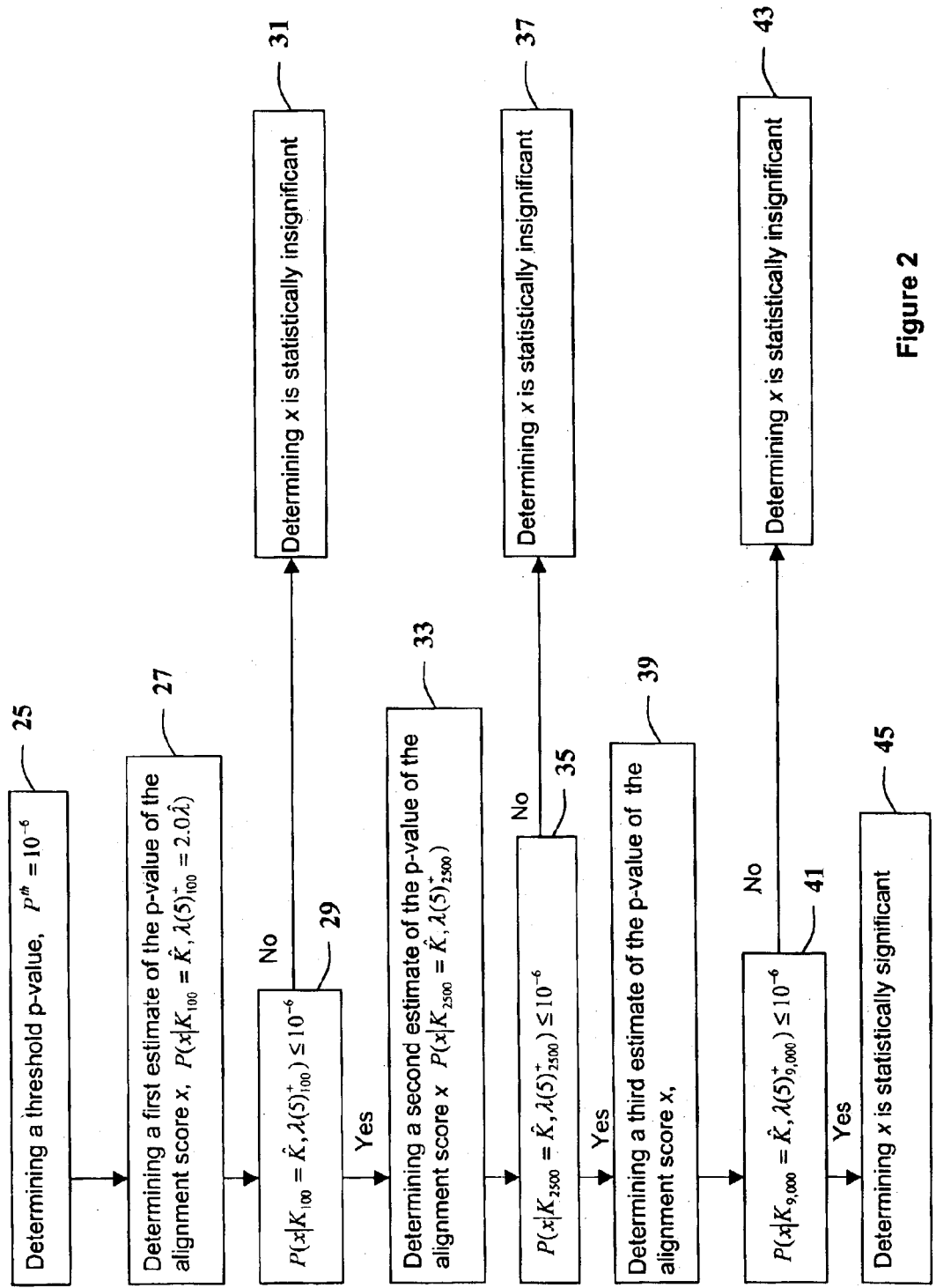
FIG. 2—illustrates a particular implementation of the method illustrated in FIG. 1.

The following example, illustrated in FIG. 2 will illustrate how the methods according to the invention illustrated in FIG. 1 may be applied to determine whether those raw alignment scores produced from aligning a query sequence to each template sequence in a large database comprising 1,000,0000 template are statistically significant or insignificant without the use of look-up tables. Assume that a raw alignment score x is determined by aligning the query sequence to a first template sequence. Still, further assume that in first step 25, a threshold p-value is selected as $10^{-6}$ so that the normalized alignment score reported are sensitive to distantly related template sequences.

A second step 27 determines a first estimate of the p-value of the raw alignment score x, $P(x|K_{100}=\hat{K},\lambda(5)_{100}^+=2.0\hat{\lambda})$, for N=100 islands and j=5. N=100 is initially chosen because of the limited computational burden imposed by generating 100 islands. Assuming typical PSI-BLAST gap scoring schemes, 100 islands may be generated by less than 10 sequence randomizations and in many cases less than 5 sequence randomizations. A third step 29 compares $P(x|K_{100}=\hat{K},\lambda(5)_{100}^+=2.0\hat{\lambda})$ to $10^{-6}$. If 31 $P(x|K_{100}=\hat{K},\lambda(5)_{100}^+=2.0\hat{\lambda}) > 10^{-6}$, the raw alignment score between the query sequence and the first template sequence may be disregarded as statistically insignificant and the raw alignment score for the query sequence and second template sequence may be calculated. Thus, with very few sequence randomizations and accordingly, a minimal computational burden, even a first estimate of the p-value of a raw alignment score in combination with observation 1 may be used to quickly determine whether a raw alignment score is statistically insignificant with a <<<1% error rate.

If $P(x|K_{100}=\hat{K},\lambda(5)_{100}^+=2.0\hat{\lambda}) \leq 10^{-6}$, a fourth step 33 determines a second estimate of the p-value of the raw alignment score x, $P(x|K_{2500}=\hat{K},\lambda(5)_{2500}^+=1.11\hat{\lambda})$ for N=2500 and j=5. A fifth step 35, compares $P(x|K_{2500}=\hat{K},\lambda(5)_{2500}^+=1.11\hat{\lambda})$ using the same comparison rules as used in step 4. If 37 $P(x|K_{2500}=\hat{K},\lambda(5)_{2500}^+=1.11\hat{\lambda}) > 10^{-6}$, the raw alignment score may be considered statistically insignificant. If $P(x|K_{2500}=\hat{K},\lambda(5)_{2500}^+=1.11\hat{\lambda}) \leq 10^{-6}$, a sixth step 39 determines a third estimate of the p-value of the raw alignment score x, $P(x|K_{9,000}=\hat{K},\lambda(5)_{9,000}^+ \approx \lambda_{true})$ for N=9,000 and j=5. A seventh step 41 compares $P(x|K_{9,000}=\hat{K},\lambda(5)_{9,000}^+ \approx \lambda_{true})$ to $10^{-6}$. If 45 $P(x|K_{9,000}=\hat{K},\lambda(5)_{9,000}^+ \approx \lambda_{true}) \leq 10^{-6}$, the raw alignment score may be considered statistically significant, if 43 $P(x|K_{9,000}=\hat{K},\lambda(5)_{9,000}^+ \approx \lambda_{true}) > 10^{-6}$, it may be considered statistically insignificant.

Another normalization method according to the invention that depends upon estimating p-values based upon jointly varying $\lambda$ and K may be developed using observations 4 and 6. Since for these cases the estimates of the p-value of raw alignment score x treat both $\lambda$ and K as variables, $P(x|K, \lambda)$ shall be rewritten as $P(x|K(\lambda(j)_N^{\pm})_N^{\pm}, \lambda(j)_N^{\pm})$. This method, illustrated in FIG. 3, comprises the steps of: 1) determining 51 a threshold p-value, $P^{th}$; 2) determining 53 a first estimate of the p-value of the raw alignment score x, $P(x|K(\lambda(j)_{N_1}^+)_{N_1}^-, \lambda(j)_{N_1}^+)$; 3) comparing 55 $P(x|K(\lambda(j)_{N_1}^+)_{N_1}^-, \lambda(j)_{N_1}^+)$ to $P^{th}$; 4) if 59 $P(x|K(\lambda(j)_{N_1}^+)_{N_1}^-, \lambda(j)_{N_1}^+) \leq P^{th}$ determining a second estimate of the p-value of the raw alignment score x, $P(x|K(\lambda(j)_{N_2}^+)_{N_2}^-, \lambda(j)_{N_2}^+)$, where $N_2 \geq N_1$, otherwise 57, determining the alignment score x is statistically insignificant; 5) repeating 61 steps 3) and 4) until determining a final estimate of the p-value of raw alignment score x, $P(x|K(\lambda(j)_{N_{final}}^+)_{N_{final}}^-, \lambda(j)_{N_{final}}^+)$; 6) comparing 67 $P(x|K(\lambda(j)_{N_{final}}^+)_{N_{final}}^-, \lambda(j)_{N_{final}}^+)$ to $P^{th}$; and 7) if 71 $P(x|K(\lambda(j)_{N_{final}}^+)_{N_{final}}^-, \lambda(j)_{N_{final}}^+) \leq P^{th}$, determining the raw alignment score x is statistically significant, otherwise 69, determining it is statistically insignificant. While, one skilled in the art will certainly appreciate that in general, $K(\lambda(j))_{N_1}^-$ and $\lambda(j)_{N_1}^+$ may be represented more generally as $K(\lambda(j))_{N_{1,K}}^-$ and $\lambda(j)_{N_{1,\lambda}}^+$ since it is not necessary that $N_{1,K} = N_{1,\lambda}$, for the sake of clarity of presentation, the case of $N_{1,K} = N_{1,\lambda} = N_1$ will be illustrated.

EXAMPLE 2

Figure 3:
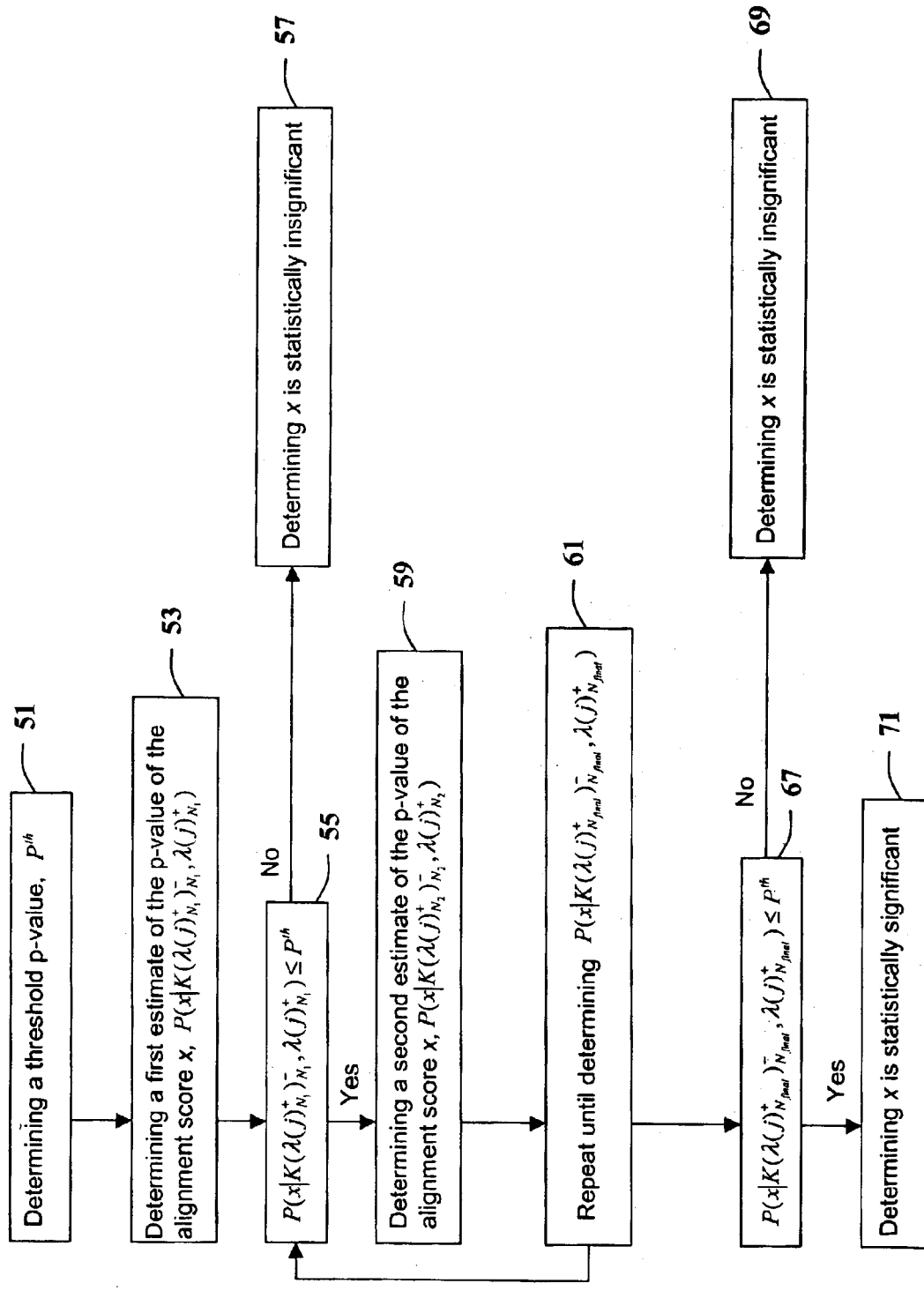
FIG. 3—illustrates a further method according to the invention for quickly determining the statistical significance or insignificance of a raw alignment score produced by aligning a first sequence to a second sequence.
Figure 4:
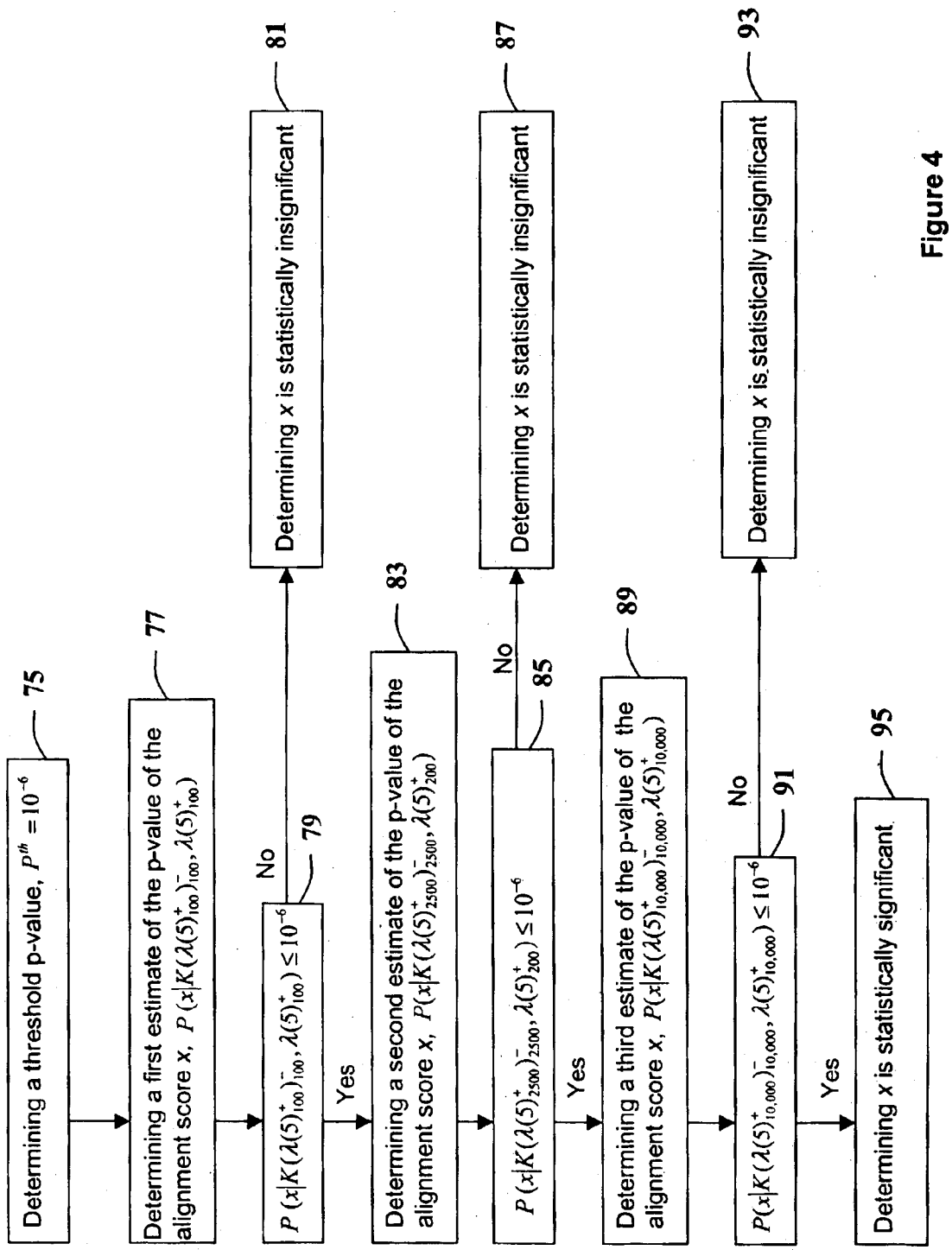
FIG. 4—illustrates a particular implementation of the method illustrated in FIG. 3.

The following example, illustrated in FIG. 4 will illustrate how the claimed methods, based on the inequalities in observation 4 and 6, and illustrated in FIG. 3, may be applied to determine the statistical significance or insignificance of the raw alignment scores produced by aligning a query sequence to each template sequence in a large template sequence database. Once again, assume that a raw alignment score x is determined by aligning the query sequence to a first template sequence and that the template database comprises 1,000,000 sequences. Further assume that in first step 75, a threshold p-value is selected as $10^{-6}$ so that the normalized alignment scores reported are sensitive to distantly related template sequences. A second step 77 determines a first estimate of the p-value of the raw alignment score x, $P(x|K(\lambda(5)_{100}^+)_{100}^-, \lambda(5)_{100}^+)$, for N=100 islands and j=5. A third step 79, compares $P(x|K(\lambda(5)_{100}^+)_{100}^-, \lambda(5)_{100}^+)$ to $10^{-6}$. If 81 $P(x|K(\lambda(5)_{100}^+)_{100}^-, \lambda(5)_{100}^+) > 10^{-6}$ the raw alignment score between the query sequence and the first template sequence may be disregarded as statistically insignificant and the raw alignment score for the query sequence and second template sequence may be calculated. Thus, with very few sequence randomizations and accordingly, a minimal computational burden, even a first estimate of the p-value of a raw alignment score in combination with observation 1 may be used to determine quickly determine whether a raw alignment score is statistically insignificant with a <<<1% error rate.

If 83 $P(x|K(\lambda(5)_{100}^+)_{100}^-, \lambda(5)_{100}^+) \leq 10^{-6}$, a fourth step determines a second estimate of the p-value of raw alignment score x, $P(x|K(\lambda(5)_{2500}^+)_{2500}^-, \lambda(5)_{200}^+)$, for N=2500 and j=5. A fifth step 85, compares $P(x|K(\lambda(5)_{2500}^+)_{2500}^-, \lambda(5)_{200}^+)$ to $10^{-6}$ using the same comparison rules as used in step 4. Consequently, if $P(x|K(\lambda(5)_{2500}^+)_{2500}^-, \lambda(5)_{200}^+) \leq 10^{-6}$, a sixth step 89 determines a third estimate and final of the p-value of the raw alignment score x, $P(x|K(\lambda(5)_{10,000}^+)_{10,000}^-, \lambda(5)_{10,000}^+)$ for N=10,000 and j=5. Otherwise 87, the raw alignment score x is considered statistically insignificant. A seventh step 91, compares $P(x|K(\lambda(5)_{10,000}^+)_{10,000}^-, \lambda(5)_{10,000}^+)$ to $10^{-6}$. If 95 $P(x|K(\lambda(5)_{10,000}^+)_{10,000}^-, \lambda(5)_{10,000}^+) \leq 10^{-6}$, the raw alignment score x is considered statistically significant, otherwise 93, it is considered statistically insignificant.

There is no inherent limitation on the number of the estimates of the p-value of a raw alignment score that may be employed by the methods illustrated in FIGS. 3–4. The number of p-value estimates that may be employed depends upon the size of the database search, the require sensitivity and the available computational resources. Typically two to about ten p-value estimates may be employed. But, given sufficient computational resources thousands of estimates may be determined. Most of the sequences screened in a database will have no statistically meaningful alignment with a query sequence and the first estimate of the p-value of a raw alignment score may serve as a useful filter for quickly determining many such statistically insignificant scores at a low computational overhead.

This suggests another method according to the invention. By performing steps 2–4, namely, determining estimates of the p-value of a raw alignment score from $P(x|K(\lambda(j)_{N_1}^+)_{N_1}^-, \lambda(j)_{N_1}^+)$ and comparing that estimate to a threshold p-value, it is possible to rapidly determine whether a raw alignment score is statistically insignificant. More generally, steps 2–3 may be repeated a plurality of times with each estimate of the p-value being determined from a larger number of islands than the preceding estimate of the p-value.

It also follows that it is more computationally efficient to increase N non-linearly so that the first few p-value estimates use less than approximately 3,500 islands. Although in the case of only two estimates of the p-value being computed, the first estimate, $P(x|K(\lambda(j)_{N_1}^+)_{N_1}^-, \lambda(j)_{N_1}^+)$ may be determined from even 5000 islands.

Figure 5:
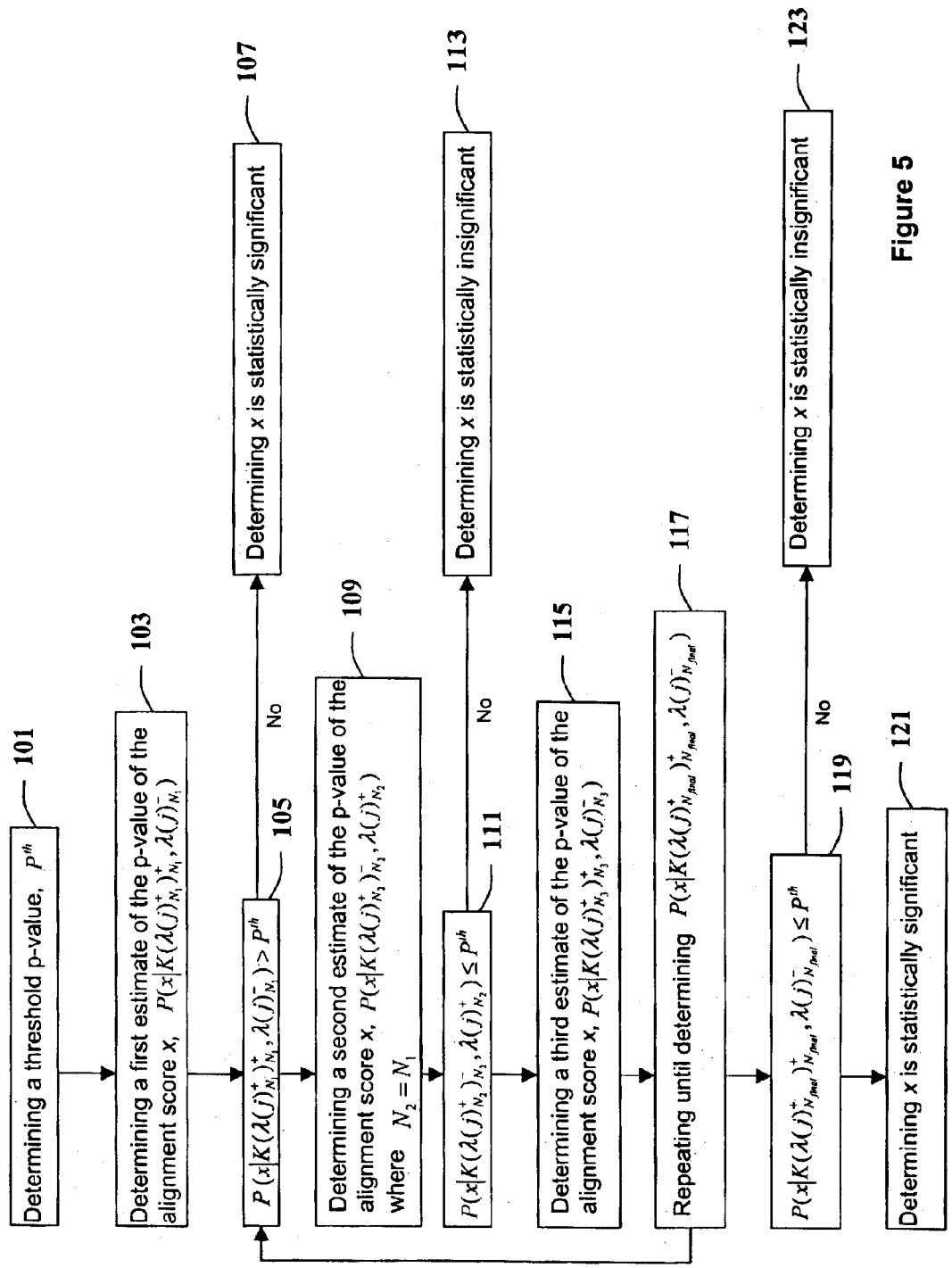
FIG. 5—illustrates a still further method according to the invention for quickly determining the statistical significance or insignificance of a raw alignment score produced by aligning a first sequence to a second sequence.

The inequalities in observations 4 and 6 permit other methods, illustrated in FIG. 5, for quickly determining the statistical in/significance of a raw alignment score comprising the steps of: 1) determining 101 a threshold p-value, $P^{th}$; 2) determining 103 a first estimate of the p-value of the raw alignment score x, $P(x|K(\lambda(j)_{N_1}^+)_{N_1}^+, \lambda(j)_{N_1}^-)$; 3) comparing 105 $P(x|K(\lambda(j)_{N_1}^+)_{N_1}^+, \lambda(j)_{N_1}^-)$; to $P^{th}$; 4) if 109 $P(x|K(\lambda(j)_{N_1}^+)_{N_1}^+, \lambda(j)_{N_1}^-) > P^{th}$ determining a second estimate of the p-value of the raw alignment score x, $P(x|K(\lambda(j)_{N_2}^-)_{N_2}^-, \lambda(j)_{N_2}^+)$ where $N_2 = N_1$, otherwise 107, determining that the raw alignment score is statistically significant; 5) comparing 111 $P(x|K(\lambda(j)_{N_2}^+)_{N_2}^-, \lambda(j)_{N_2}^+)$ to $P^{th}$; 6) if 115 $P(x|K(\lambda(j)_{N_2}^+)_{N_2}^-, \lambda(j)_{N_2}^+) \leq P^{th}$ determining a third estimate of the p-value of the raw alignment score x, $P(x|K(\lambda(j)_{N_3}^+)_{N_3}^+, \lambda(j)_{N_3}^-)$, where $N_3 \geq N_1$, otherwise 113, determining the raw alignment score is statistically insignificant; 7) repeating 117 steps 3) through 6) until determining a final estimate of the p-value of raw alignment score x, $P(x|K(\lambda(j)_{N_{final}}^+)_{N_{final}}^+, \lambda(j)_{N_{final}}^-)$; 8) comparing 119 $P(x|K(\lambda(j)_{N_{final}}^+)_{N_{final}}^+, \lambda(j)_{N_{final}}^-)$ to $P^{th}$; and 9) if 121 $P(x|K(\lambda(j)_{N_{final}}^+)_{N_{final}}^+, \lambda(j)_{N_{final}}^-) \leq P^{th}$, determining the raw alignment score x, is statistically significant, otherwise 123, determining it is insignificant. While one skilled in the art will certainly appreciate that in general, $K(\lambda(j))_{N_1}^{\pm}$ and $\lambda(j)_{N_1}^{\pm}$ may be, represented more generally as $K(\lambda(j)_{N_{1,K}}^{\pm}$ and $\lambda(j)_{N_{1,\lambda}}^{\pm}$ since it is not necessary that $N_{1,K} = N_{1,\lambda}$, for the sake of clarity of presentation, the case of $N_{1,K} = N_{1,\lambda} = N_1$ will be illustrated in the following example.

EXAMPLE 3

Figure 6:
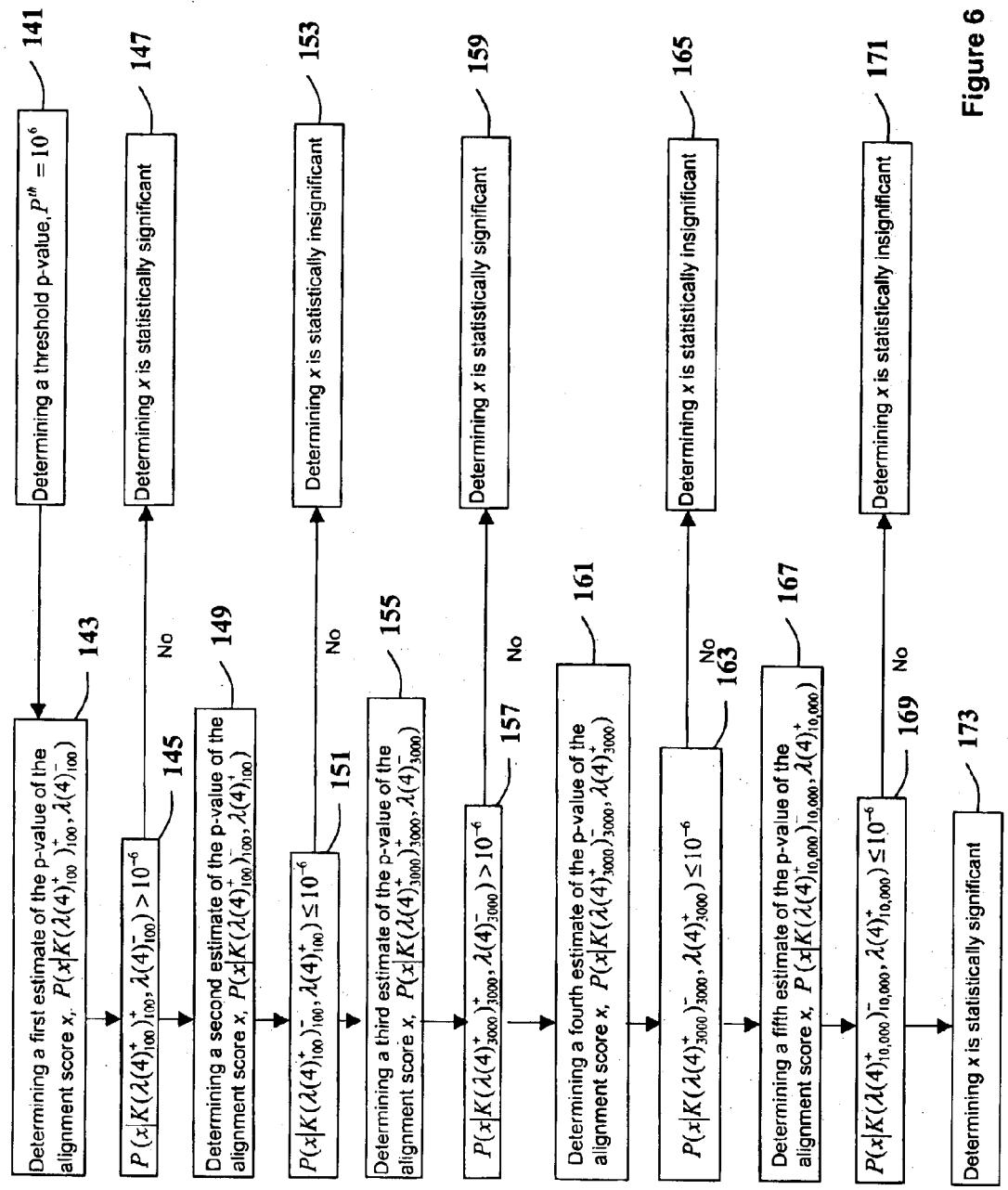
FIG. 6—illustrates a particular implementation of the method illustrated in FIG. 5.

The following example, illustrated in FIG. 6, will show how the methods detailed immediately above and illustrated in FIG. 5 may be applied to determine the statistical significance or insignificance of the raw alignment scores produced by aligning a query sequence to a database of 1,000,000 template sequences. Once again, it shall be assumed that a raw alignment score x is determined by aligning the query sequence to a first template sequence. Further assume that in a first step 141, a threshold p-value is selected as $P^{th}=10^{-6}$.

A second step 143 determines a first estimate of the p-value of the raw alignment score x, $P(x|K(\lambda(4)_{100}^+)_{100}^+, \lambda(4)_{100}^-)$ for N=100 islands and j=4. A third step 145, compares $P(x|K(\lambda(4)_{100}^+)_{100}^+\lambda(4)_{100}^-)$ to $10^{-6}$. If 149 $P(x|K(\lambda(4)_{100}^+)_{100}^+,\lambda(4)_{100}^-)>10^{-6}$, a fourth step calculates a second estimate of the p-value of the raw alignment score x, $P(x|K(\lambda(4)_{100}^+)_{100}^-,\lambda(4)_{100}^+)$ for the same N=100 islands used in the second step and j=4. If 147 $P(x|K(\lambda(4)_{100}^+)_{100}^+, \lambda(4)_{100}^-) \leq 10^{-6}$, the raw alignment score may be considered statistically significant and the raw alignment score for the query sequence and second template sequence may be calculated. A fifth step 151, compares $P(x|K(\lambda(4)_{100}^+)_{100}^-, \lambda(4)_{100}^+)$ to $10^{-6}$. If 153 $P(x|K(\lambda(4)_{100}^+)_{100}^-,\lambda(4)_{100}^+)>10^{-6}$, the raw alignment score between the query sequence and the first template sequence may be considered statistically insignificant. If 155 $P(x|K(\lambda(4)_{100}^+)_{100}^-,\lambda(4)_{100}^+) \leq 10^{-6}$ a sixth step calculates a third estimate of the p-value of raw alignment score x, $P(x|K(\lambda(4)_{3000}^+)_{3000}^+,\lambda(4)_{3000}^-)$ for N=3000 islands and j=4.

A seventh step 157, compares $P(x|K(\lambda(4)_{3000}^+)_{3000}^+,\lambda(4)_{3000}^-)$ to $10^{-6}$. If 159 $P(x|K(\lambda(4)_{3000}^+)_{3000}^+,\lambda(4)_{3000}^-) \leq 10^{-6}$ the raw alignment score between the query sequence and the first template sequence may be considered statistically significant and the raw alignment score for the query sequence and second template sequence may be calculated.

If 161 $P(x|K(\lambda(4)_{3000}^+)_{3000}^+,\lambda(4)_{3000}^-)>10^{-6}$, an eighth step determines a fourth estimate of the p-value of raw alignment score x, $P(x|K(\lambda(4)_{3000}^+)_{3000}^-,\lambda(4)_{3000}^+)$. A ninth step 163 compares $P(x|K(\lambda(4)_{3000}^+)_{3000}^-,\lambda(4)_{3000}^+)$ to $10^{-6}$. If 167 $P(x|K(\lambda(4)_{3000}^+)_{3000}^-,\lambda(4)_{3000}^+) \leq 10^{-6}$, a ten step determines a fifth and final estimate of the p-value of the alignment score x, $P(x|K(\lambda(4)_{10,000}^+)_{10,000}^-,\lambda(4)_{10,000}^+)$ for N=10,000 and j=4. If 165 $P(x|K(\lambda(4)_{3000}^+)_{3000}^-,\lambda(4)_{3000}^+) > 10^{-6}$, the raw alignment score x, is considered statistically insignificant.

Since for N=10,000, $P(x|K(\lambda(4)_{10,000}^+)_{10,000}^-,\lambda(4)_{10,000}^+) \approx P(x|K(\lambda(4)_{10,000}^+)_{10,000}^+,\lambda(4)_{10,000}^-) \approx P(x|K_{true}\lambda_{true})$. An eleventh step 169 compares $P(x|K(\lambda(4)_{10,000}^+)_{10,000}^-,\lambda(4)_{10,000}^+)$ to $10^{-6}$. If 173 $P(x|K(\lambda(4)_{10,000}^+)_{10,000}^-,\lambda(4)_{10,000}^+) \leq 10^{-6}$, the raw alignment score produced by aligning the query sequence and the first template sequence may be considered statistically significant, otherwise 171, the raw alignment score may be considered statistically insignificant and the raw alignment score for the query sequence and second template sequence may be calculated.

There is no inherent limitation on the number of the estimates of the p-value of a raw alignment score that may be employed by the methods illustrated in FIGS. 5–6. The number of p-value estimates that may be employed by claimed methods depends upon the available computational resources, the size of the database and the sensitivity of the search. Typically two to about ten p-value estimates may be employed. But, given sufficient computational resources thousands of estimates may be determined. Most of the sequences screened in a database will have no statistically meaningful alignment with a query sequence and the first estimate of the p-value of a raw alignment score may serve as a useful filter for quickly determining many such statistically insignificant scores at a low computational overhead.

This suggests another method according to the invention. By performing steps 2–4, namely, determining estimates of the p-value of a raw alignment score, from $P(x|K(\lambda(j)_{N_1}^+)_{N_1}^+,\lambda(j)_{N_1}^-)$, and comparing that estimate to a threshold p-value, it is possible to rapidly determine whether a raw alignment score is statistically significant. More generally, steps 2–4 may be repeated a plurality of times with each estimate of the p-value being determined from a larger number of islands than the preceding estimate of the p-value. Similarly, this suggests yet another method according to the invention. By performing steps 3–5, namely, determining estimates of the p-value of a raw alignment score, from $P(x|K(\lambda(j)_{N_1}^+)_{N_1}^-,\lambda(j)_{N_1}^+)$, and comparing that estimate to a threshold p-value, it is possible to rapidly determine whether a raw alignment score is statistically insignificant. More generally, steps 3–5 may be repeated a plurality of times with each estimate of the p-value being determined from a larger number of islands than the preceding estimate of the p-value.

It also follows that it is more computationally efficient to increase N non-linearly so that the first few p-value estimates use less than approximately 3,500 islands. Although in the case of only two estimates of the p-value being computed, the first estimate, $P(x|K(\lambda(j)_{N_1}^+)_{N_1}^+,\lambda(j)_{N_1}^-)$ may be determined from even 5000 islands.

Systems According to the Invention

Figure 7:
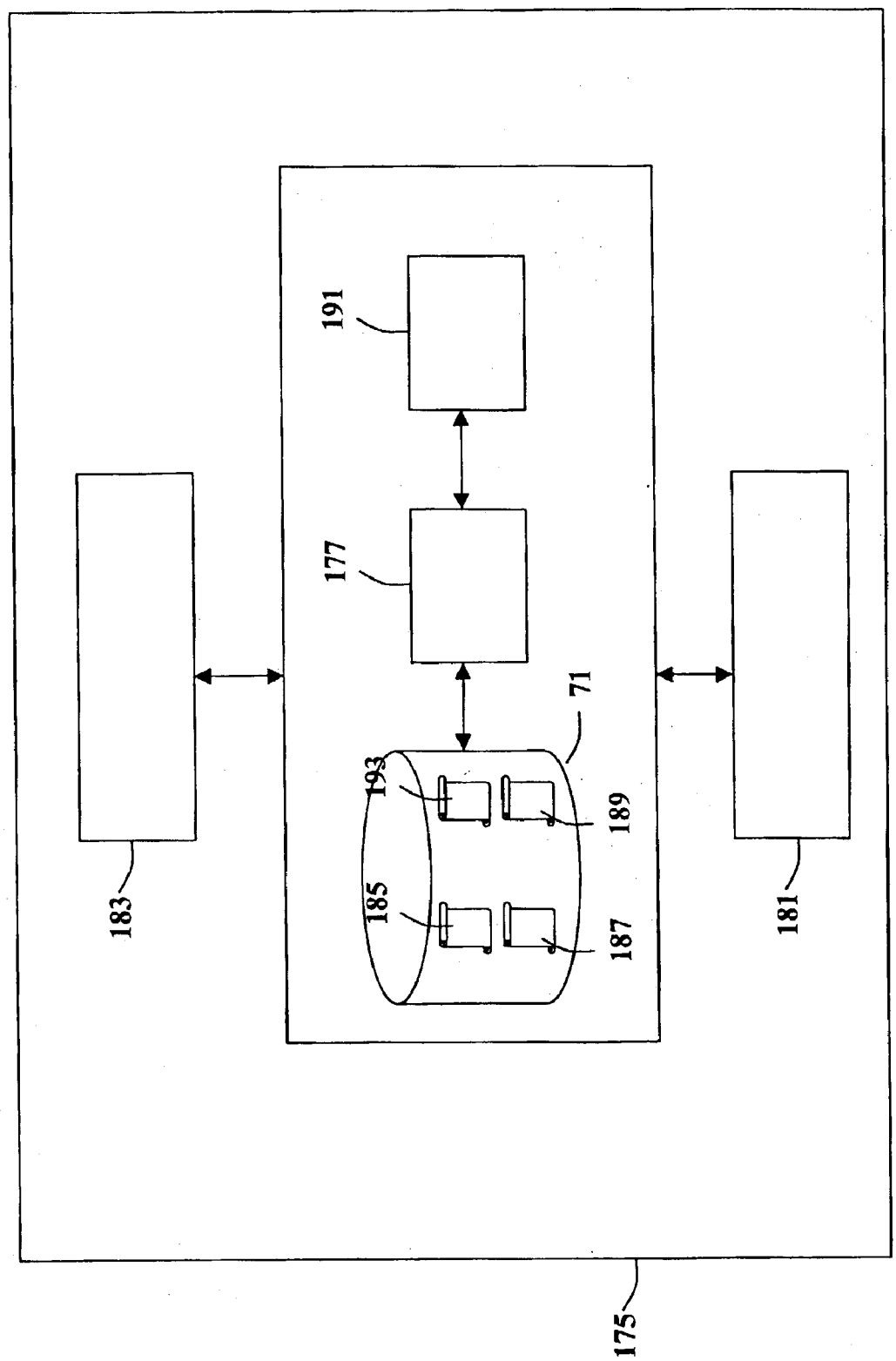
FIG. 7—illustrates a general hardware architecture for the systems according to the invention.

In general, as is shown in FIG. 7, a system according to the invention 175 comprises a processor 177, a memory 179, an input 181, an output device 183, programming for an operating system 185, programming for determining sequence alignment scores 187, programming for storing and retrieving a plurality of sequences and alignment scores 193, and programming for the methods according to the invention 189. The systems according to the invention may optionally, also comprise a system for networking to another device 191.

A processor 177 may include one or more microprocessor(s), field programmable logic array(s), or one or more application specific integrated circuit(s). Exemplary processors include Intel Corp.'s Pentium series processor (Santa Clara, Calif.), Motorola Corp.'s PowerPC processors (Schaumberg, Ill.), MIPS Technologies Inc.'s MIPs processors (Mountain View, Calif.), or Xilinx Inc.'s Vertex series of field programmable logic arrays (San Jose, Calif.).

A memory 179 includes any electronic, magnetic or optical based media for storing digital information or a combination of such media. Exemplary types of memory include random access memory, electronically programmable read only memory, flash memory magnetic based disk and tape drives, and optical based disk drives. The memory stores the programming for the methods according to the invention.

An input device 181 may include a keyboard and mouse or a touch screen/tablet or some combination thereof.

An output device 183 may include one or more visual displays and or printers. A visual display may be based upon any monitor technology known in the art including, cathode ray tube based monitors/projectors, plasma based monitors, liquid crystal display based monitors, digital micro-mirror device based projectors, or lightvalve based projectors.

Programming for an operating system 185 comprises machine code for controlling the data flow between the processor, memory, input device, and the output device. Exemplary operating systems include Microsoft Corp's Windows and NT (Redmond, Wash.), Sun Microsystem Inc.'s Solaris Operating System (Palo Alto, Calif.), Red Hat Corp.'s version of Linux (Durham, N.C.) and Palm Corp.'s PALM OS (Milpitas, Calif.).

Programming for determining sequence alignment scores 187 comprises machine code for determining sequence alignment scores and may be based upon the BLAST, PSI-BLAST or HMM algorithms. Baxevanis, A., Ouellette, B. F., *Bioinformatics, A Practical Guide to the Analysis of Genes and Proteins* (Wiley Interscience, 2001).

Programming for the methods according to the invention 189 comprises machine code for performing the methods according to the invention.

A networking system 191 comprises the hardware and software to allow a system according to the invention to electronically communicate to another device. Exemplary networking schemes may be based on packet over any media including Ethernet 10/1000, IEEE 802.11x, IEEE 1394, xDSL, Bluetooth, or any other ANSI approved standard.

Programming 193 for storing and retrieving a plurality sequences and alignment scores includes relational and object oriented databases such as Oracle Corp.'s 9i (Redwood City, Calif.), International Business Machine's DB2 (Armronk, N.Y.), Microsoft Corp.'s Access (Redmond, Wash.) and Versant's Corp.'s (Freemont, Calif.) Versant Developer Suite 6.0. If alignment calculations and sequences are stored as flat files, programming for storing and retrieving of alignment calculations also includes operating systems.

Systems according to the invention may be based upon PCs and network servers programmed to perform the methods according to the invention. A suitable server and hardware configuration is a enterprise class Pentium based server, comprising an operating system such as Microsoft's NT, Sun Microsystems' Solaris or Red Hat's version of Linux with 1 GB random access memory, 100 GB storage, an enterprise class database, TCP/IP enabled, either a line area network communications card, such as a 10/100 Ethernet card or a high speed Internet connection, such as an enterprise T1/E1 line or an xDSL line, an enterprise database comprising a plurality of sequences, sequence alignment scoring software, such as PSI-BLAST, and programming for the methods according to the invention. The storage and memory requirements listed above are not intended to represent minimum hardware configurations, rather they represent a typical server system which may readily purchased from vendors at the time of filing. Such servers may be readily purchased from Dell, Inc. (Austin, Tex.), or Hewlett-Packard, Inc., (Palo Alto, Calif.) with all the features except for the enterprise database, the PSI-BLAST source code and the programming for the methods according to the invention. The source code for PSI-BLAST may be downloaded for free at www.ncbi.nlm.nih.gov and installed on an enterprise server. Enterprise database may be purchased from Oracle Corp or International Business Machines, Inc.

A suitable desktop PC and hardware configuration is a Pentium based desktop computer comprising at least 128 MB of random access memory, 10 GB of storage, either a line area network communications card, such as a 10/100 Ethernet card or a high speed Internet connection, such as an enterprise T1/E1 line or an xDSL line, a TCP/IP web browser, such as Microsoft's Internet Explorer, a database such as Microsoft's Access comprising a plurality of sequences, sequence alignment scoring software, such as PSI-BLAST, and programming for the methods according to the invention. Once again, the exemplary storage and memory requirement are only intended to represent PC configurations which are readily available from vendors at the time of filing. They are not intended to represent minimum configurations. Such PCs may be readily purchased from Dell, Inc. or Hewlett-Packard, Inc., (Palo Alto, Calif.) with all the features except for the PSI-BLAST software and the programming for the protein sorting methods according to the invention. The source code for PSI-BLAST may be downloaded for free at www.ncbi.nlm.nih.gov and installed on a desktop PC.

Although the invention has been described with reference to preferred embodiments and specific examples, it will be readily appreciated by those skilled in the art that many modifications and adaptations of the invention are possible without deviating from the spirit and scope of the invention. Thus, it is to be clearly understood that this description is made only by way of example and not as a limitation on the scope of the invention as claimed below.

What is claimed is:

1. A method for determining whether an alignment score x, determined from the alignment of a first sequence with a second sequence, is statistically insignificant comprising the steps of:
  a. determining a threshold p-value, $P^{th}$;
  b. determining a first estimate of the p-value of said alignment score x, $P(x|K_{N_{1,K}}, \lambda(j)_{N_{1,\lambda}}{}^+)$, using the Island method wherein $K_{N_{1,K}}$ is determined using $N_{1,K}$ islands, $\lambda(j)_{N_{1,\lambda}}{}^+$ is determined using $N_{1,\lambda}$ islands and $j \geq 3$;
  c. comparing $P(x|K_{N_{1,K}}, \lambda(j)_{N_{1,\lambda}}{}^+)$ to $P^{th}$; and
  d. if $P(x|K_{N_{1,K}}, \lambda(j)_{N_{1,\lambda}}{}^+) > P^{th}$, determining said alignment score is statistically insignificant, otherwise, determining said alignment score may or may not be statistically insignificant.

2. The method of claim 1 wherein $N_{1,K}$, $N_{1,\lambda}$ are each less than 5000.

3. The method of claim 1 wherein $N_{1,K}$, $N_{1,\lambda}$ are each less than 3000.

4. The method of claim 1 wherein $N_{1,K}$, $N_{1,\lambda}$ are each less than 1000.

5. The method of claim 1 wherein $N_{1,K}$, $N_{1,\lambda}$ are each less than 500.

6. A method for determining whether an alignment score x, determined from the alignment of a first sequence with a second sequence, is statistically significant or insignificant comprising the steps of:
  a. determining a threshold p-value, $P^{th}$;
  b. determining a first estimate of the p-value of said alignment score x, $P(x|K_{N_{1,K}}, \lambda(j)_{N_{1,\lambda}}{}^+)$, using the Island method wherein $K_{N_{1,K}}$ is determined using $N_{1,K}$ islands, $\lambda(j)_{N_{1,\lambda}}{}^+$ is determined using $N_{1,\lambda}$ islands and $j \geq 3$;
  c. comparing $P(x|K_{N_{1,K}}, \lambda(j)_{N_{1,\lambda}}{}^+)$ to $P^{th}$;
  d. if $P(x|K_{N_{1,K}}, \lambda(j)_{N_{1,\lambda}}{}^+) \leq P^{th}$, determining a second estimate of the p-value of said alignment score x, $P(x|K_{N_{2,K}}, \lambda(j)_{N_{2,\lambda}}{}^+)$ using the Island method wherein $K_{N_{2,K}}$ is determined using $N_{2,K} \geq 9000$ islands, $\lambda(j)_{N_{2,\lambda}}{}^+$ is determined using $N_{2,\lambda} \geq 9000$ islands and $j \geq 3$, otherwise, determining said alignment score x is statistically insignificant;
  e. comparing $P(x|K_{N_{2,K}}, \lambda(j)_{N_{2,\lambda}}{}^+)$ to $P^{th}$; and
  f. if $P(x|K_{N_{2,K}}, \lambda(j)_{N_{2,\lambda}}{}^+) \leq P^{th}$, determining said alignment score is statistically significant, otherwise, determining said alignment score is statistically insignificant.

7. The method of claim 6 wherein $N_{1,K}$, $N_{1,\lambda}$ are each less than 5000.

8. The method of claim 6 wherein $N_{1,K}$, $N_{1,\lambda}$ are each less than 3000.

9. The method of claim 6 wherein $N_{1,K}$, $N_{1,\lambda}$ are each less than 1000.

10. The method of claim 6 wherein $N_{1,K}$, $N_{1,\lambda}$ are each less than 500.

11. A method for determining whether an alignment score x, determined from the alignment of a first sequence with a second sequence, is statistically significant or insignificant comprising the steps of:
   a. determining a threshold p-value, $P^{th}$;
   b. determining a first estimate of the p-value of said alignment score x, $P(x|K_{N_{1,K}}, \lambda(j)_{N_{1,\lambda}}^+)$, using the Island method wherein $K_{N_{1,K}}$ is determined using $N_{1,K}$ islands, $\lambda(j)_{N_{1,\lambda}}^+$ is determined using $N_{1,\lambda}$ islands and $j \geq 3$;
   c. comparing $P(x|K_{N_{1,K}}, \lambda(j)_{N_{1,\lambda}}^+)$ to $P^{th}$;
   d. if $P(x|K_{N_{1,K}}, \lambda(j)_{N_{1,\lambda}}^+) \leq P^{th}$, determining a second estimate of the p-value of said alignment score x, $P(x|K_{N_{2,K}}, \lambda(j)_{N_{2,\lambda}}^+)$, using the Island method wherein $K_{N_{2,K}}$ is determined using $N_{2,K}$ islands, $\lambda(j)_{N_{2,\lambda}}^+$ is determined using $N_{2,\lambda}$ islands and $j \geq 3$, otherwise, determining said alignment score x is statistically insignificant;
   e. repeating steps c) and d) until determining a final estimate of the p-value of said alignment score, $P(x|K_{N_{final,K}}, \lambda(j)_{N_{final,\lambda}}^+)$, using the, Island method wherein $K_{N_{final,K}}$ is determined using $N_{final,K} \geq 9000$ islands, $\lambda(j)_{N_{final,\lambda}}^+$ is determined using $N_{final,\lambda} \geq 9000$ islands and $j \geq 3$;
   f. comparing $P(x|K_{N_{final,K}}, \lambda(j)_{N_{final,\lambda}}^+)$ to $P^{th}$; and
   g. if $P(x|K_{N_{final,K}}, \lambda(j)_{N_{final,\lambda}}^+) \leq P^{th}$ determining said alignment score x is statistically significant, otherwise determining said alignment score x is statistically insignificant.

12. The method of claim 11 wherein $N_{1,K}$, $N_{1,\lambda}$ are each less than 3000.

13. The method of claim 11 wherein $N_{1,K}$, $N_{1,\lambda}$ are each less than 1000.

14. The method of claim 11 wherein $N_{1,K}$, $N_{1,\lambda}$ are each less than 500.

15. A method for determining whether an alignment score x, determined from the alignment of a first sequence with a second sequence, is statistically significant or insignificant comprising the steps of:
   a. determining a threshold p-value, $P^{th}$;
   b. determining a first estimate of the p-value of said alignment score x, $P(x|K_{N_1}, \lambda(j)_{N_1}^+)$, using the Island method wherein $K_{N_1}$ and $\lambda(j)_{N_1}^+$ are each determined using $N_1$ islands and $j > 3$;
   c. comparing $P(x|K_{N_1}, \lambda(j)_{N_1}^+)$ to $P^{th}$;
   d. if $P(x|K_{N_1}, \lambda(j)_{N_1}^+) \leq P^{th}$, determining a second estimate of the p-value of said alignment score x, $P(x|K_{N_2}, \lambda(j)_{N_2}^+)$, using the Island method wherein $K_{N_2}$ and $\lambda(j)_{N_2}^+$ are each determined using $N_2$ islands and $j \geq 3$, otherwise, determining said alignment score x is statistically insignificant;
   e. repeating steps c) and d) until determining a final estimate of the p-value of said alignment score, $P(x|K_{N_{final}}, \lambda(j)_{N_{final}}^+)$, using the Island method wherein $K_{N_{final}}$ and $\lambda(j)_{N_{final}}^+$ are each determined using $N_{final} \geq 9000$ islands and $j \geq 3$, otherwise;
   f. comparing $P(x|K_{N_{final}}, \lambda(j)_{N_{final}}^+)$ to $P^{th}$; and
   g. if $P(x|K_{N_{final}}, \lambda(j)_{N_{final}}^+) \leq P^{th}$, determining said alignment score x is statistically significant, otherwise determining said alignment score x is statistically insignificant.

16. The method of claim 15 wherein $N_1$ is less than 1000.

17. The method of claim 15 wherein $N_1$ is less than 500.

18. A method for determining whether an alignment score x, determined from the alignment of a first sequence with a second sequence, is statistically insignificant comprising the steps of:
   a. determining a threshold p-value, $P^{th}$;
   b. determining a first estimate of the p-value of said alignment score x, $P(x|K(\lambda(j)_{N_{1,\lambda}}^+)_{N_{1,K}}^-, \lambda(j)_{N_{1,\lambda}}^+)$, using the Island method wherein $K(\lambda(j)_{N_{1,\lambda}}^+)_{N_{1,K}}^-$ is determined using $N_{1,K}$ islands, $\lambda(j)_{N_{1,\lambda}}^+$ is determined using $N_{1,\lambda}$ islands and $j \geq 3$;
   c. comparing $P(x|K(\lambda(j)_{N_{1,\lambda}}^+)_{N_{1,K}}^-, \lambda(j)_{N_{1,\lambda}}^+)$ to $P^{th}$; and
   d. if $P(x|K(\lambda(j)_{N_{1,\lambda}}^+)_{N_{1,K}}^-, \lambda(j)_{N_{1,\lambda}}^+) > P^{th}$, determining said alignment score x is statistically insignificant, otherwise, determining said alignment score may or may not be statistically insignificant.

19. The method of claim 18 wherein $N_{1,K}$, $N_{1,\lambda}$ are each less than 5000.

20. The method of claim 18 wherein $N_{1,K}$, $N_{1,\lambda}$ are each less than 3000.

21. The method of claim 18 wherein $N_{1,K}$, $N_{1,\lambda}$ are each less than 1000.

22. The method of claim 18 wherein $N_{1,K}$, $N_{1,\lambda}$ are each less than 500.

23. A method for determining whether an alignment score x, determined from the alignment of a first sequence with a second sequence, is statistically significant or insignificant comprising the steps of:
   a. determining a threshold p-value, $P^{th}$;
   b. determining a first estimate of the p-value of said alignment score x, $P(x|K(\lambda(j)_{N_{1,\lambda}}^+)_{N_{1,K}}^-, \lambda(j)_{N_{1,\lambda}}^+)$, using the Island method wherein $K(\lambda(j)_{N_{1,\lambda}}^+)_{N_{1,K}}^-$ is determined using $N_{1,K}$ islands, $\lambda(j)_{N_{1,\lambda}}^+$ is determined using $N_{1,\lambda}$ islands and $j \geq 3$;
   c. comparing $P(x|K(\lambda(j)_{N_{1,\lambda}}^+)_{N_{1,K}}^-, \lambda(j)_{N_{1,\lambda}}^+)$ to $P^{th}$;
   d. if $P(x|K(\lambda(j)_{N_{1,\lambda}}^+)_{N_{1,K}}^-, \lambda(j)_{N_{1,\lambda}}^+) \leq P^{th}$, determining a second estimate of the p-value to said alignment score x, $P(x|K(\lambda(j)_{N_{2,\lambda}}^+)_{N_{2,K}}^-, \lambda(j)_{N_{2,\lambda}}^+)$, using the Island method wherein $K(\lambda(j)_{N_{2,\lambda}}^+)_{N_{2,K}}^-$ is determined using $N_{2,K} \geq 9000$ islands, $\lambda(j)_{N_{2,\lambda}}^+$ is determined using $N_{2,\lambda} 9000$ islands and $j \geq 3$, otherwise, determining said alignment score x is statistically insignificant;
   e. comparing $P(x|K(\lambda(j)_{N_{2,\lambda}}^+)_{N_{2,K}}^-, \lambda(j)_{N_{2,\lambda}}^+)$ to $P^{th}$; and
   f. if $P(x|K(\lambda(j)_{N_{2,\lambda}}^+)_{N_{2,K}}^-, \lambda(j)_{N_{2,\lambda}}^+) \leq P^{th}$, determining said alignment score x is statistically significant, otherwise determining said alignment score x is statistically insignificant.

24. The method of claim 23 wherein $N_{1,K}$, $N_{1,\lambda}$ are each less than 5000.

25. The method of claim 23 wherein $N_{1,K}$, $N_{1,\lambda}$ are each less than 3000.

26. The method of claim 23 wherein $N_{1,K}$, $N_{1,\lambda}$ are each less than 1000.

27. The method of claim 23 wherein $N_{1,K}$, $N_{1,\lambda}$ are each less than 500.

28. A method for determining whether an alignment score x, determined from the alignment of a first sequence with a second sequence, is statistically significant or insignificant comprising the steps of:
   a. determining a threshold p-value, $P^{th}$;
   b. determining a first estimate of the p-value of said alignment score x $P(x|K(\lambda(j)_{N_{1,\lambda}}^+)_{N_{1,K}}^-, \lambda(j)_{N_{1,\lambda}}^+)$, using the Island method wherein $K(\lambda(j)_{N_{1,\lambda}}^+)_{N_{1,K}}^-$ is determined using $N_{1,K}$ islands, $\lambda(j)_{N_{1,\lambda}}^+$ is determined using $N_{1,\lambda}$ islands and $j \geq 3$;
   c. comparing $P(x|K(\lambda(j)_{N_{1,\lambda}}^+)_{N_{1,K}}^-, \lambda(j)_{N_{1,\lambda}}^+)$ to $P^{th}$;
   d. if $P(x|K(\lambda(j)_{N_{1,\lambda}}^+)_{N_{1,K}}^-, \lambda(j)_{N_{1,\lambda}}^+) \leq P^{th}$, determining a second estimate of the p-value to said alignment score x, $P(x|K(\lambda(j)_{N_{2,\lambda}}^+)_{N_{2,K}}^-, \lambda(j)_{N_{2,\lambda}}^+)$, using the Island method wherein $K(\lambda(j)_{N_{2,\lambda}}^+)_{N_{2,K}}^-$ is determined using $N_{2,K}$ islands, $\lambda(j)_{N_{2,\lambda}}^+$ is determined using $N_{2,\lambda}$ islands and $j \geq 3$, otherwise, determining said alignment score x is statistically insignificant;

e. repeating steps c) and d) until determining a final estimate of the p-value of said alignment score x, $P(x|K(\lambda(j)_{N_{final,\lambda}}^+)_{N_{final,K}}^- \lambda(j)_{N_{final,\lambda}}^+)$, using the Island method wherein $K(\lambda(j)_{N_{final,\lambda}}^+)_{N_{final,K}}^-$ is determined using $N_{final,K} \geq 9000$ islands, $\lambda(j)_{N_{final,\lambda}}^+$ is determined using $N_{final,\lambda} \geq 9000$ islands and $j \geq 3$;

f. comparing $P(x|K(\lambda(j)_{N_{final,\lambda}}^+)_{N_{final,K}}^- \lambda(j)_{N_{final,\lambda}}^+)$ to $P^{th}$; and g. if $P(x|K(\lambda(j)_{N_{final,\lambda}}^+)_{N_{final,K}}^- \lambda(j)_{N_{final,\lambda}}^+) \leq P^{th}$ determining said alignment score x is statistically significant, otherwise determining said alignment score x is statistically insignificant.

29. The method of claim 28 wherein $N_{1,K}$, $N_{1,\lambda}$ are each less than 3000.

30. The method of claim 28 wherein $N_{1,K}$, $N_{1,\lambda}$ are each less than 1000.

31. The method of claim 28 wherein $N_{1,K}$, $N_{1,\lambda}$ are each less than 500.

32. A method for determining whether an alignment score x, determined from the alignment of a first sequence with a second sequence, is statistically significant or insignificant comprising the steps of:

a. determining a threshold p-value, $P^{th}$;

b. determining a first estimate of the p-value of said alignment score x $P(x|K(\lambda(j)_{N_1}^+)_{N_1}^- \lambda(j)_{N_1}^+)$, using the Island method wherein $K(\lambda(j)_{N_1}^+)_{N_1}^-$ and $\lambda(j)_{N_1}^+$ are each determined using $N_1$ islands and $j \geq 3$;

c. comparing $P(x|K(\lambda(j)_{N_1}^+)_{N_1}^- \lambda(j)_{N_1}^+)$ to $P^{th}$;

d. if $P(x|K(\lambda(j)_{N_1}^+)_{N_1}^- \lambda(j)_{N_1}^+) \leq P^{th}$, determining a second estimate of the p-value to said alignment score x, $P(x|K(\lambda(j)_{N_2}^+)_{N_2}^- \lambda(j)_{N_2}^+)$ using the Island method wherein $K(\lambda(j)_{N_2}^+)_{N_2}^-$ and $\lambda(j)_{N_2}^+$ are each determined using $N_2$ islands and $j \geq 3$, otherwise, determining said alignment score x is statistically insignificant;

e. repeating steps c) and d) until determining a final estimate of the p-value of said alignment score x, $P(x|K(\lambda(j)_{N_{final}}^+)_{N_{final}}^- \lambda(j)_{N_{final}}^+)$, using the Island method wherein $K(\lambda(j)_{N_{final}}^+)_{N_{final}}^-$ and $\lambda(j)_{N_{final}}^+$ are each determined using $N_{final} \geq 9000$ islands and $j \geq 3$;

f. comparing $P(x|K(\lambda(j)_{N_{final}}^+)_{N_{final}}^- \lambda(j)_{N_{final}}^+)$ to $P^{th}$; and g. if $P(x|K(\lambda(j)_{N_{final}}^+)_{N_{final}}^- \lambda(j)_{N_{final}}^+) \leq P^{th}$ determining said alignment score x is statistically significant, otherwise determining said alignment score x is statistically insignificant.

33. The method of claim 32 wherein $N_1$ is less than 1000.

34. The method of claim 32 wherein $N_1$ is less than 500.

35. A method for determining whether an alignment score x, determined from the alignment of a first sequence with a second sequence, is statistically significant or insignificant comprising the steps of:

a. determining a threshold p-value, $P^{th}$;

b. determining a first estimate of the p-value of said alignment score x $P(x|K(\lambda(j)_{N_{1,\lambda}}^+)_{N_{1,K}}^+ \lambda(j)_{N_{1,\lambda}}^-)$, using the Island method wherein $K(\lambda(j)_{N_{1,\lambda}}^+)_{N_{1,K}}^+$ is determined using $N_{1,K}$ islands, $\lambda(j)_{N_{1,\lambda}}^-$ and $\lambda(j)_{N_{1,\lambda}}^+$ are each determined using $N_{1,\lambda}$ islands and $j \geq 3$;

c. comparing $P(x|K(\lambda(j)_{N_{1,\lambda}}^+)_{N_{1,K}}^+ \lambda(j)_{N_{1,\lambda}}^-)$ to $P^{th}$;

d. if $P(x|K(\lambda(j)_{N_{1,\lambda}}^+))_{N_{1,K}}^+ \lambda(j)_{N_{1,\lambda}}^-) > P^{th}$, determining a second estimate of the p-value to said alignment score x, $P(x|K(\lambda(j)_{N_{2,\lambda}}^+)_{N_{2,K}}^- \lambda(j)_{N_{2,\lambda}}^+)$, using the Island method wherein $K(\lambda(j)_{N_{2,\lambda}}^+)_{N_{2,K}}^-$ is determined using $N_{2,K}=N_{1,K}$ islands, $\lambda(j)_{N_{2,\lambda}}^+$ is determined using $N_{2,\lambda}=N_{1,\lambda}$ islands and $j \geq 3$, otherwise, determining said alignment score x is statistically significant;

e. comparing $P(x|K(\lambda(j)_{N_{2,\lambda}}^+)_{N_{2,K}}^- \lambda(j)_{N_{1,\lambda}}^+)$ to $P^{th}$;

f if $P(x|K(\lambda(j)_{N_{2,\lambda}}^+)_{N_{2,K}}^-, \lambda(j)_{N_{1,\lambda}}^+) \leq P^{th}$, determining a third estimate of the p-value of said alignment score x, $P(x|K(\lambda(j)_{N_{3,\lambda}}^+)_{N_{3,K}}^+ \lambda(j)_{N_{3,\lambda}}^-)$ using the Island method wherein $K(\lambda(j)_{N_{3,\lambda}}^+)_{N_{3,K}}^+$ is determined using, $N_{3,\lambda} \geq 9$,000 islands, $\lambda(j)_{N_{3,\lambda}}^-$ and $\lambda(j)_{N_{3,\lambda}}^+$ are each determined using $N_{3,\lambda} \geq 9,000$ islands and $j \leq 3$, otherwise, determining said alignment score x is statistically insignificant;

g. comparing $P(x|K(\lambda(j)_{N_{3,\lambda}}^+)_{N_{3,K}}^+ \lambda(j)_{N_{3,\lambda}}^-)$ to $P^{th}$; and h. if $P(x|K(\lambda(j)_{N_{3,\lambda}}^+)_{N_{3,K}}^+ \lambda(j)_{N_{3,\lambda}}^-) \leq P^{th}$, determining said alignment score x is statistically significant, otherwise, determining said alignment score x is statistically insignificant.

36. The method of claim 35 wherein $N_{1,K}$, $N_{1,\lambda}$ are each less than 5000.

37. The method of claim 35 wherein $N_{1,K}$, $N_{1,\lambda}$ are each less than 3000.

38. The method of claim 35 wherein $N_{1,K}$, $N_{1,\lambda}$ are each less than 1000.

39. The method of claim 35 wherein $N_{1,K}$, $N_{1,\lambda}$ are each less than 500.

40. A method for determining whether an alignment score x, determined from the alignment of a first sequence with a second sequence, is statistically significant or insignificant comprising the steps of:

a. determining a threshold p-value, $P^{th}$;

b. determining a first estimate of the p-value of said alignment score x $P(x|K(\lambda(j)_{N_{1,\lambda}}^+)_{N_{1,K}}^+ \lambda(j)_{N_{1,\lambda}}^-)$, using the Island method wherein $K(\lambda(j)_{N_{1,\lambda}}^+)_{N_{1,K}}^+$ is determined using $N_{1,K}$ islands, $\lambda(j)_{N_{1,\lambda}}^-$ and $\lambda(j)_{N_{1,\lambda}}^+$ are each determined using $N_{1,\lambda}$ islands and $j \leq 3$;

c. comparing $P(x|K(\lambda(j)_{N_{1,\lambda}}^+)_{N_{1,K}}^+ \lambda(j)_{N_{1,\lambda}}^-)$ to $P_{th}$;

d. if $P(x|K(\lambda(j)_{N_{1,\lambda}}^+)_{N_{1,K}}^+ \lambda(j)_{N_{1,\lambda}}^-) > P^{th}$, determining a second estimate of the p-value of said alignment score x, $P(x|K(\lambda(j)_{N_{2,\lambda}}^+)_{N_{2,K}}^- \lambda(j)_{N_{2,\lambda}}^+)$, using the Island method wherein $K(\lambda(j)_{N_{2,\lambda}}^+)_{N_{2,K}}^-$ is determined using $N_{2,K}=N_{1,K}$ islands, $\lambda(j)_{N_{2,\lambda}}^+$ is determined using $N_{2,\lambda}=N_{1,\lambda}$ islands and $j \geq 3$, otherwise, determining said alignment score x is statistically significant;

e. comparing $P(x|K(\lambda(j)_{N_{2,\lambda}}^+)_{N_{2,K}}^- \lambda(j)_{N_{2,\lambda}}^+)$ to $P^{th}$;

f. if $P(x|K(\lambda(j)_{N_{2,\lambda}}^+)_{N_{2,K}}^- \lambda(j)_{N_{2,\lambda}}^+) \leq P^{th}$, determining a third estimate of the p-value of said alignment score x, $P(x|K(\lambda(j)_{N_{3,\lambda}}^+)_{N_{3,K}}^+ \lambda(j)_{N_{3,\lambda}}^-)$, using the Island method wherein $K(\lambda(j)_{N_{3,\lambda}}^+)_{N_{3,K}}^+$ is determined using $N_{3,K}$ islands, $\lambda(j)_{N_{3,\lambda}}^+$ and $\lambda(j)_{N_{3,\lambda}}^-$ are each determined using $N_{3,\lambda}$ islands and $j \geq 3$, otherwise, determining said alignment score x is statistically insignificant;

g. repeating steps c)–f) until determining a final estimate of the p-value of said alignment score x, $P(x|K(\lambda(j)_{N_{final,\lambda}}^+)_{N_{final,K}}^+ \lambda(j)_{N_{final,\lambda}}^-)$, using the Island method wherein $K(\lambda(j)_{N_{final,\lambda}}^+)_{N_{final,K}}^+$ is determined using $N_{final,K} \geq 9000$ islands, $\lambda(j)_{N_{final,\lambda}}^-$ and $\lambda(j)_{N_{final,\lambda}}^+$ are each determined using $N_{final,\lambda} \geq 9000$ islands and $j \geq 3$;

h. comparing $P(x|K(\lambda(j)_{N_{final,\lambda}}^+))_{N_{final,K}}^+ \lambda(j)_{N_{final,\lambda}}^-)$ to $P^{th}$; and i. if $P(x|K(\lambda(j)_{N_{final,\lambda}}^+)_{N_{final,K}}^+ \lambda(j)_{N_{final,\lambda}}^-) \leq P^{th}$, determining said alignment score x is statistically significant, otherwise determining said alignment score x is statistically insignificant.

41. The method of claim 40 wherein $N_{1,K}$, $N_{1,\lambda}$ are each less than 3000.

42. The method of claim 40 wherein $N_{1,K}$, $N_{1,\lambda}$ are each less than 1000.

43. The method of claim 40 wherein $N_{1,K}$, $N_{1,\lambda}$ are each less than 500.

44. A method for determining whether an alignment score x, determined from the alignment of a first sequence with a second sequence, is statistically significant or insignificant comprising the steps of:

a. determining a threshold p-value, $P^{th}$;

b. determining a first estimate of the p-value of said alignment score x $P(x|K(\lambda(j)_{N_1}^+)_{N_1}^+,\lambda(j)_{N_1}^-)$, using the Island method wherein $K(\lambda(j)_{N_1}^+)_{N_1}^+,\lambda(j)_{N_1}^+)$ and $\lambda(j)_{N_1}^-$ are each determined using $N_1$ islands and $j \geq 3$;

c. comparing $P(x|K(\lambda(j)_{N_1}^+)_{N_1}^+,\lambda(j)_{N_1}^-)$ to $P^{th}$;

d. if $P(x|K(\lambda(j)_{N_1}^+)_{N_1}^+,\lambda(j)_{N_1}^-) > P^{th}$, determining a second estimate of the p-value of said alignment score x, $P(x|K(\lambda(j)_{N_2}^+)_{N_2}^-,\lambda(j)_{N_2}^+)$, using the Island method wherein $K(\lambda(j)_{N_2}^+)_{N_2}^-$ and $\lambda(j)_{N_2}^+$ are each determined using $N_2 = N_1$, islands and $j \geq 3$, otherwise, determining said alignment score x is statistically significant;

e. comparing $P(x|K(\lambda(j)_{N_2}^+)_{N_2}^-,\lambda(j)_{N_2}^+)$ to $P^{th}$;

f. if $P(x|K(\lambda(j)_{N_2}^+)_{N_2}^-,\lambda(j)_{N_2}^+) \leq P^{th}$, determining a third estimate of the p-value of said alignment score x, $P(x|K(\lambda(j)_{N_3}^+)_{N_3}^+,\lambda(j)_{N_3}^-)$, using the Island method wherein $K(\lambda(j)_{N_3}^+)_{N_3}^+,\lambda(j)_{N_3}^+$ and $\lambda(j)_{N_3}^-$ are each determined using $N_3$ islands and $j \geq 3$, otherwise, determining said alignment score x is statistically insignificant;

g. repeating steps c)–f) until determining a final estimate of the p-value of said alignment score x, $P(x|K(\lambda(j)_{N_{final}}^+)_{N_{final}}^+,\lambda(j)_{N_{final}}^-)$, using the Island method wherein $K(\lambda(j)_{N_{final}}^+)_{N_{final}}^+,\lambda(j)_{N_{final}}^-$ and $\lambda(j)_{N_{final}}^-$ are each determined using $N_{final} \geq 9000$ islands and $j \geq 3$;

h. comparing $P(x|K(\lambda(j)_{N_{final}}^+)_{N_{final}}^+,\lambda(j)_{N_{final}}^-)$ to $P^{th}$; and i. if $P(x|K(\lambda(j)_{N_{final}}^+)_{N_{final}}^+,\lambda(j)_{N_{final}}^-) \leq P^{th}$, determining said alignment score x is statistically significant, otherwise, determining said alignment score x is statistically insignificant.

45. The method of claim 44 wherein $N_1$ is less than 1000.

46. The method of claim 44 wherein $N_1$ is less than 500.

47. A computer system comprising:
a. an input device;
b. an output device;
c. a processor;
d. a memory;
e. programming for an operating system;
f. programming for determining sequence alignment scores;
g. programming for storing and retrieving a plurality of sequences and sequence alignment scores; and
h. programming for the method of claim 2.

48. A computer system comprising:
a. an input device;
b. an output device;
c. a processor;
d. a memory;
e. programming for an operating system;
f. programming for determining sequence alignment scores;
g. programming for storing and retrieving a plurality of sequences and sequence alignment scores; and
h. programming for the method of claim 7.

49. A computer system comprising:
a. an input device;
b. an output device;
c. a processor;
d. a memory;
e. programming for an operating system;
f. programming for determining sequence alignment scores;
g. programming for storing and retrieving a plurality of sequences and sequence alignment scores; and
h. programming for the method of claim 12.

50. A computer system comprising:
a. an input device;
b. an output device;
c. a processor;
d. a memory;
e. programming for an operating system;
f. programming for determining sequence alignment scores;
g. programming for storing and retrieving a plurality of sequences and sequence alignment scores; and
h. programming for the method of claim 17.

51. A computer system comprising:
a. an input device;
b. an output device;
c. a processor;
d. a memory;
e. programming for an operating system;
f. programming for determining sequence alignment scores;
g. programming for storing and retrieving a plurality of sequences and sequence alignment scores; and
h. programming for the method of claim 19.

52. A computer system comprising:
a. an input device;
b. an output device;
c. a processor;
d. a memory;
e. programming for an operating system;
f. programming for determining sequence alignment scores;
g. programming for storing and retrieving a plurality of sequences and sequence alignment scores; and
h. programming for the method of claim 24.

53. A computer system comprising:
a. an input device;
b. an output device;
c. a processor;
d. a memory;
e. programming for an operating system;
f. programming for determining sequence alignment scores;
g. programming for storing and retrieving a plurality of sequences and sequence alignment scores; and
h. programming for the method of claim 29.

54. A computer system comprising:
a. an input device;
b. an output device;
c. a processor;
d. a memory;
e. programming for an operating system;
f. programming for determining sequence alignment scores;

g. programming for storing and retrieving a plurality of sequences and sequence alignment scores; and h. programming for the method of claim 34.

55. A computer system comprising:

a. an input device;

b. an output device;

c. a processor;

d. a memory;

e. programming for an operating system;

f. programming for determining sequence alignment scores;

g. programming for storing and retrieving a plurality of sequences and sequence alignment scores; and h. programming for the method of claim 36.

56. A computer system comprising:

a. a. an input device;

b. an output device;

c. a processor;

d. a memory;

e. programming for an operating system;

f. programming for determining sequence alignment scores;

g. programming for storing and retrieving a plurality of sequences and sequence alignment scores; and h. programming for the method of claim 41.

57. A computer system comprising:

a. an input device;

b. an output device;

c. a processor;

d. a memory;

e. programming an operating system;

f. programming for determining sequence alignment scores;

g. programming for storing and retrieving a plurality of sequences and sequence alignment scores; and h. programming for the method of claim 46.

* * * * *